United States Patent [19]

Hasegawa et al.

[11] Patent Number: 5,808,019

[45] Date of Patent: Sep. 15, 1998

[54] INTERMEDIATE COMPOUNDS FOR THE SYNTHESIS OF GLYCOLIPIDS

[75] Inventors: Akira Hasegawa, Gifu; Makoto Kiso, Motosu-gun; Yukihiro Isogai, Gifu; Seiichi Kitamura; Hiroshi Ueda, both of Osaka, all of Japan

[73] Assignee: Toa Boshoku Kabushiki Kaisha, Japan

[21] Appl. No.: 571,512

[22] Filed: Dec. 13, 1995

[30] Foreign Application Priority Data

Dec. 19, 1994 [JP] Japan ..................... 6-340693

[51] Int. Cl.$^6$ .................................................. C07H 15/00
[52] U.S. Cl. ............................................................ 536/17.9
[58] Field of Search ........................... 536/4.1, 17.2, 536/17.9, 123.1

[56] References Cited

U.S. PATENT DOCUMENTS 4,990,604  2/1991  Ogawa et al. ..................... 536/17.9
5,567,684  10/1996  Ladisch et al. ........................ 574/25

*Primary Examiner*—Elli Peselev
*Attorney, Agent, or Firm*—Wenderoth, Lind & Ponack, L.L.P.

[57] ABSTRACT

The invention provides important intermediate compounds for the synthesis of acidic glycolipids which are identical with the glycolipid antigens isolated from the acidic glycolipid fractions of peripheral nerve and embryonic central nervous system and preparation methods thereof. By the adoption of the present intermediate compounds, sulfation of 3-hydroxyl group of end glucuronic acid portion of the acidic glycolipid can be quite easily carried out and total synthetic yield be greatly improved.

4 Claims, No Drawings

INTERMEDIATE COMPOUNDS FOR THE SYNTHESIS OF GLYCOLIPIDS

FIELD OF INVENTION

The present invention relates to intermediate compounds for the synthesis of acidic glycolipids which have the same structure with those of the glycolipid antigen isolated from the acidic glycolipid fraction of peripheral nerves and embryonic central nervous system.

BACKGROUND OF THE INVENTION

Among the membrane components detected by the monoclonal antibody preparation, attention has been concentrated into to sulfated glycolipid because its tissue distribution is the common antigen for immune cell and nervous system tissue.

Speaking of this acidic glycolipid antigen, since the same structure is included in myelin-associated glycoprotein which is an important molecular in human immune cells including human natural killer cell and nervous system, and in nerve cell adhesion molecule, great efforts have been exerted on the studies of the antigen structure and the said glycolipid antigen was issolated from the acidic glycolipid fraction of peripheral nerves and embryonic central nervous system, whose structure was determined as lacto-series glycolipid as shown below.

and antigen-antibody reactions on the cell surface and therefore, great hopes are entertained of its application studies in medicinal field. Heretofore, such glycolipid has been isolated from the extract of animal nerve cells, but is unable to be obtained in larger amounts. In Japanese Patent Application Kokai No. 223296/'91, a total synthesis of such glycolipid comprising several ten steps, starting from monosaccharide, has been reported. However, the reaction yields are not satisfactory in several steps and especially in the last step of sulfation of the end-glucuronic acid having already incorporated an expensive ceramide portion. Therefore, improvement of reaction yield has strongly been desired.

PROBLEMS TO BE SOVLED BY THE INVENTION

Therefore to establish an excellent total synthetic method of glycolipids which differs from the heretofore known method described in, for example Japanese Patent Application Kokai No.223296/91 the reaction yields in each step and especially in the last step of sulfation of the end glucuronic acid portion being far higher than those of the abovementioned Japanese Patent Application. Another object of the invention is to provide intermediate compounds which are especially useful for the synthesis of glycolipids in the present invented method.

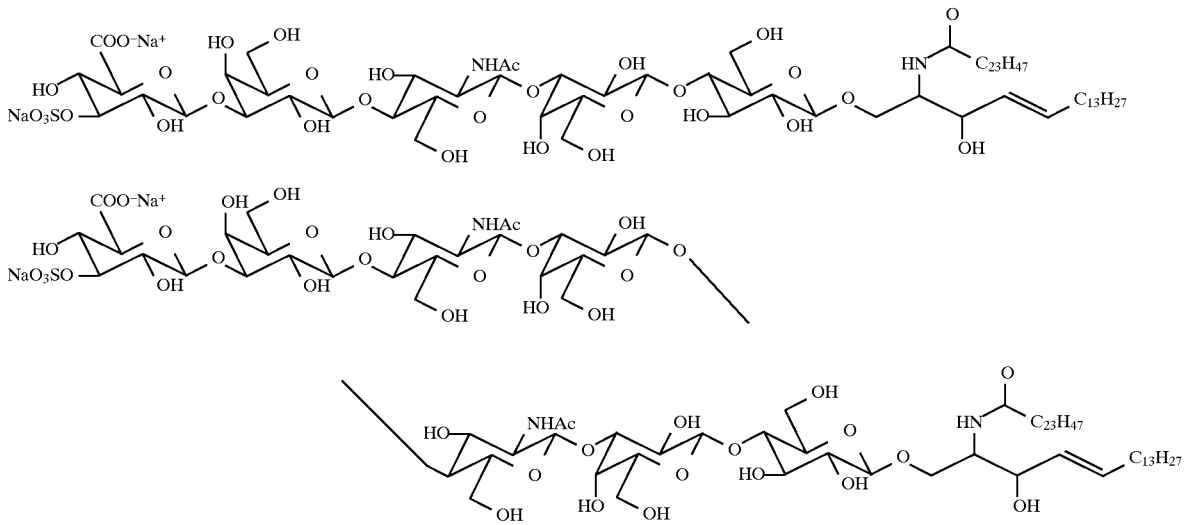

(K. H. chou et al, Biochem. Biophys. Res. Commun. 128, 383(1985);
K. H. Chou et sl J. Biol. Chem. 262, 11717(1986);
T. Ariga et sl J. Biol. Chem. 261, 848(1987))

These glycolipids are useful for elucidating biological function of sulfo-group related to the character of immunity

MEANS FOR THE SOLUTION OF THE ABOVEMENTIONED PROBLEMS

According to the invention, the abovementioned objects are attained with the following compounds. An intermediate compound for the synthesis of glycolipid, represented by the formula I

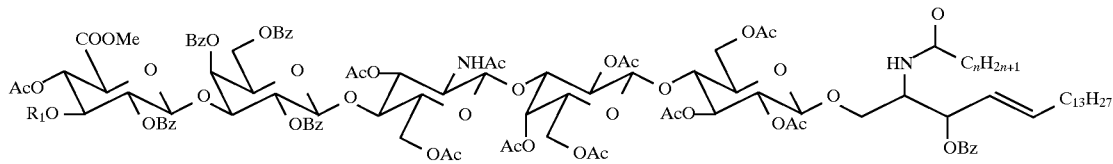

wherein R¹ represents

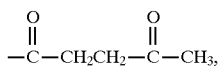

hydrogen atom or NaO₃S—; Ac stands for acetyl group; Me is methyl group; Bz is benzoyl group; and n is an integer of 17 or 23. An intermediate compound for the synthesis of glycolipid, represented by the formula II

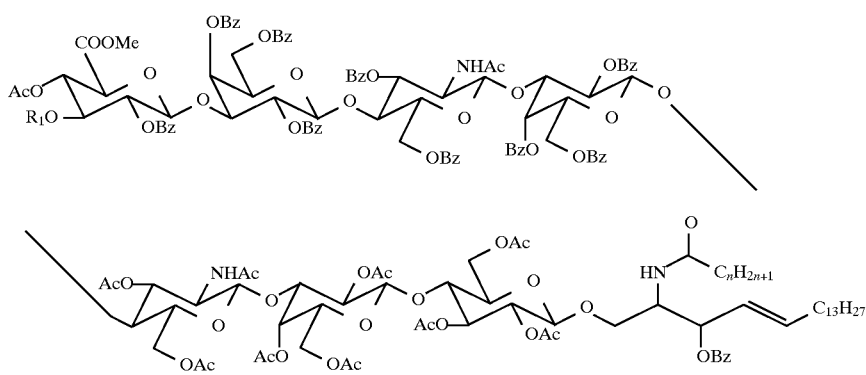

wherein R¹ represents

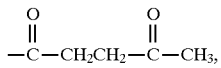

hydrogen atom or NaO₃S—; Ac stands for acetyl group; Me is methyl group; Bz is benzoyl group; and n is an integer of 17 or 23.

An intermediate compound for the synthesis of glycolipid, represented by the formula III

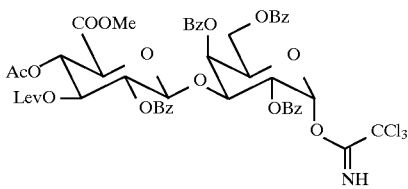

wherein Lev represents

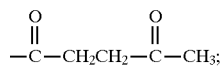

Ac stands for acetyl group; Me is methyl group; Bz is benzoyl group. An intermediate compound for the synthesis of glycolipid represented by the formula IV

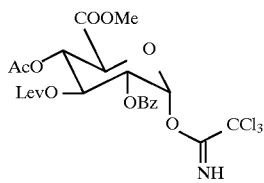

wherein Lev represents

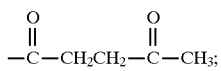

Ac stands for acetyl group; Me is methyl group; Bz is benzoyl group.

BEST MODE OF PRACTICE OF THE INVENTION

The abovementioned intermediate compounds may be advantageously prepared by the following reaction routes and converted to the final objective compounds of acidic glycolipids. However, these are only preferable reaction routes and the invention can never be limited to these routes only.

In the following, the same compound shown in the respective reaction routes each bears the same compound number.

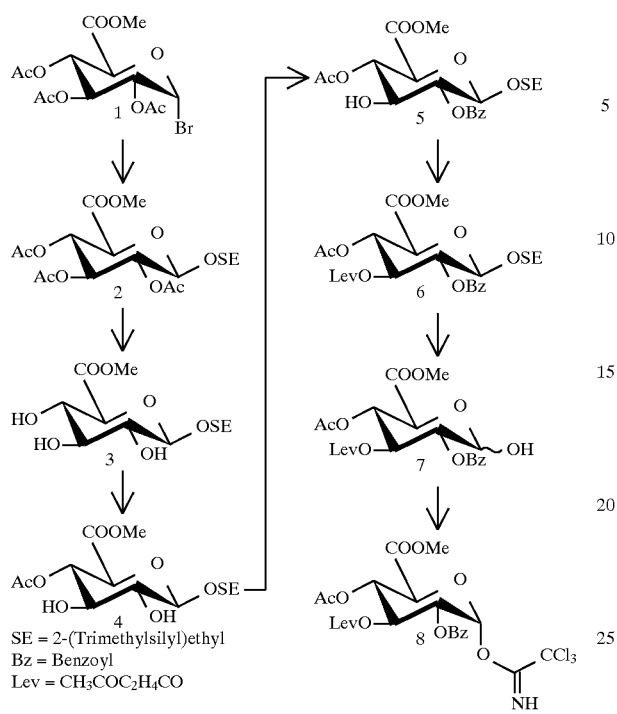

SE = 2-(Trimethylsilyl)ethyl
Bz = Benzoyl
Lev = CH₃COC₂H₄CO

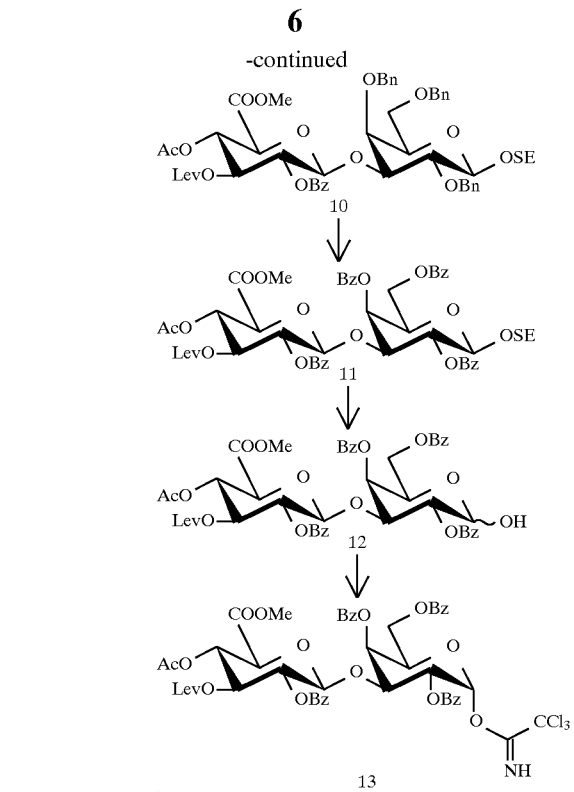

Bn = Benzyl

In this invention, starting from a known compound of methyl (tri-O-acetyl-α-D-glucopyranosyl bromide)uronate (compound 1), the 1-position of the said compound is first trimethylsilyl-ethyl-oxidized by the reaction with trimethyl silyl ethanol in the presence of silver carbonate/silver perchlorate. After removing the 2, 3 and 4-acetyl groups, only the hydroxyl group at 4-position is protected by acetyl group by the treatment with n-butyl tin oxide/methanol and subsequent reaction with acetyl chloride/triethylamine in a solvent. In the next place, after treating with n-butyl tin oxide, the hydroxyl group at 2-position is protected with benzoyl group through the reaction with benzoic anhydride, and the hydroxyl group at 3 position with levulinoyl group through the reaction with levulinic anhydride/dimethyl aminopyridine.

Thereafter, the trimethyl silyl ethyl protecting group at 1-position is removed and the thus obtained compound is reacted with trichloroacetonitrile in the presence of DBU (1, 8-diazabicyclo (4,3,0) undecene) to obtain compound 8, which is one of the present intermediate compound for the preparation of glycolipid, i.e. protected glucosyl donor, wherein 2-hydroxyl group is protected with benzoyl group, 4-hydroxyl group with acetyl group and 3-hydroxyl group with levulinoyl group and trichloroacetoimidoxy group is introduced in 1-position thereof.

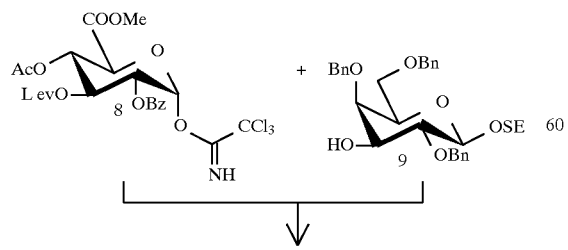

Next, the compound 8 is condensed with 2-(trimethyl silyl) ethyl-2,4,6-tri-O-benzyl-β-D-galactopyranoside (compound 9) which is a known galactose acceptor compound, by using trimethyl silyl trifluoromethane sulfonate in a solvent, thereby obtaining disaccharide compound 10. At this time, the compound 10 is obtained in as high as about 95% yield at the reaction temperature of 0° C.

The compound 10 is then derived to compound 11 by removing only the benzyl protection group through a catalytic reduction and then reacting with benzoyl chloride, wherein all of the hydroxyl groups at 2, 4 and 6-positions of the galactose are protected by benzoyl groups.

Next for the trimethyl silyl ethyl oxy group at 1-position, the same technique as stated hereinbefore is applied, thereby the trimethyl silyl ethyl protection group is removed and trichloro acetoimidation is proceeded to obtain a different intermediate compound 13 of the present invention to be used for the preparation of glycolipid, i.e. β-D-glucopyranosyl uronate -(1→3)-α-D-galactopyranosyl trichlioroacetoimide.

The compound 13 is useful as a donor compound for the reaction with hereinafter stated trisaccharide acceptor compound 20, and as the starting material for the preparation of tetra-saccharide donor compound 36.

In this invention, the trisaccharide acceptor compound is used in combination with the abovementioned donor compound and this acceptor compound 20 is prepared by the following reaction route.

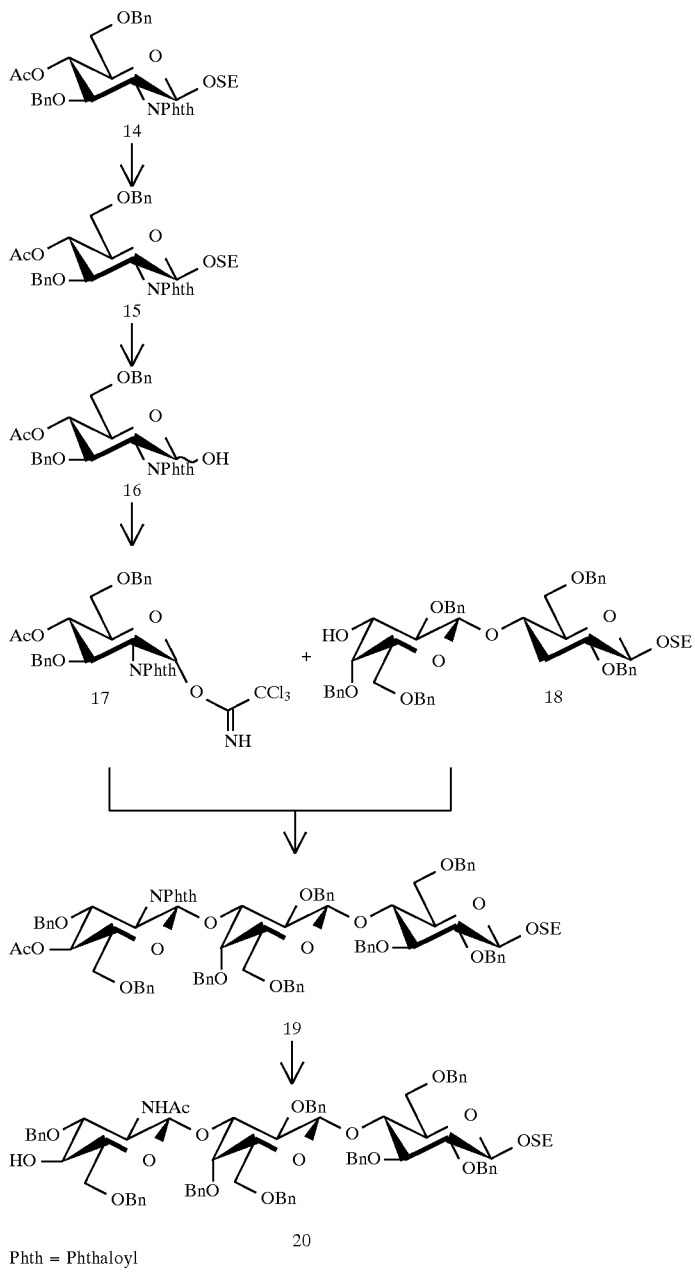

Phth = Phthaloyl

That is, starting from a known compound of 2-(trimethyl silyl)ethyl 3,6-di-O-benzyl-2-deoxy-2-phthlalimide-β-D-glutopyranoside (compound 14), 4-hydroxyl group is first protected by acetyl group through the reaction with acetic anhydride, and then 1-trimethyl silyl ethyloxy group is changed to hydroxyl group, and subsequently to trichloro-acetoimidoxy group, thereby obtaining a donor compound 17. The thus formed compound 17 is condensed with a known disaccharide acceptor compound of 2-(trimethyl silyl)ethyl O-(2,4,6-tri-O-benzyl-β-D-galactopyronosyl)-(1→4)-2,3,6-tri-O-benzyl-β-D-glucopyranoside(compound 18) in the presence of trimethyl silyl trifluoromethane sulfonate in a solvent to obtain trisaccharide compound 19. Then, the compound 19 is added with hydrazine/ethanol and thus obtained mixture is refluxed or the compound 19 is treated with sodium methoxide/methanol and subsequently with ion-exchange resin.

Thereafter, by the reaction with acetic anhydride, 4-acetyl protection group of the glucosamine ring is removed off and at the same time 2-phthlalimide protection group is changed to acetyl group, thereby obtaining the desired trisaccharide aceptor compound 20, i.e. 2-(trimethyl silyl)ethyl O-(2-acetamide-3,6,di-O-benzyl-2-deoxy-β-D-glucopyranosyl)-(1→3)-O-(2,4,6-tri-O-benzyl-β-D-galactopyranosyl)-(1→4)-2, 3, 6-tri-O-benzyl-β-D-glucopyranoside.

The other target compounds of penta saccharide glycolipid (compound 29 and 30) are advantageously prepared from the abovementioned donor compound 13 and acceptor compound 20 as follows.

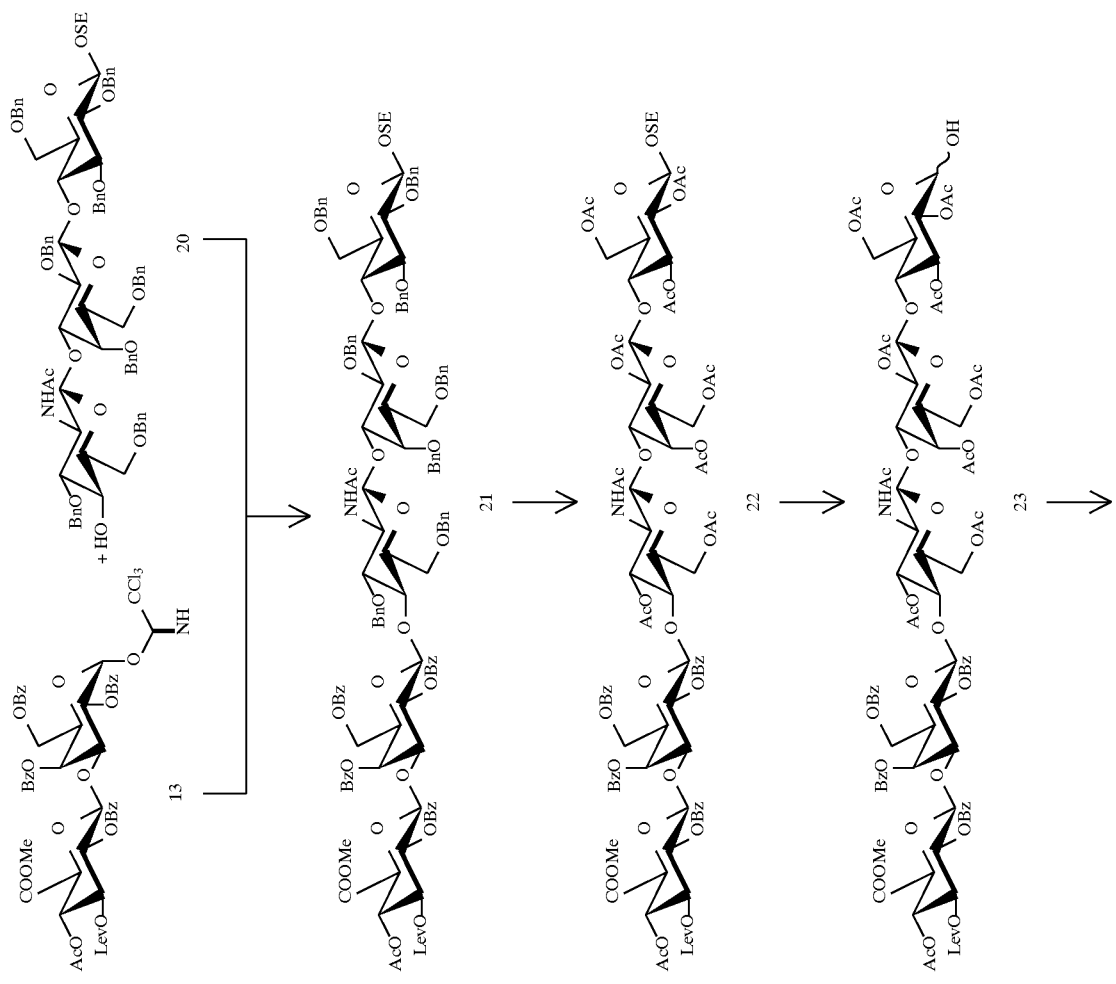

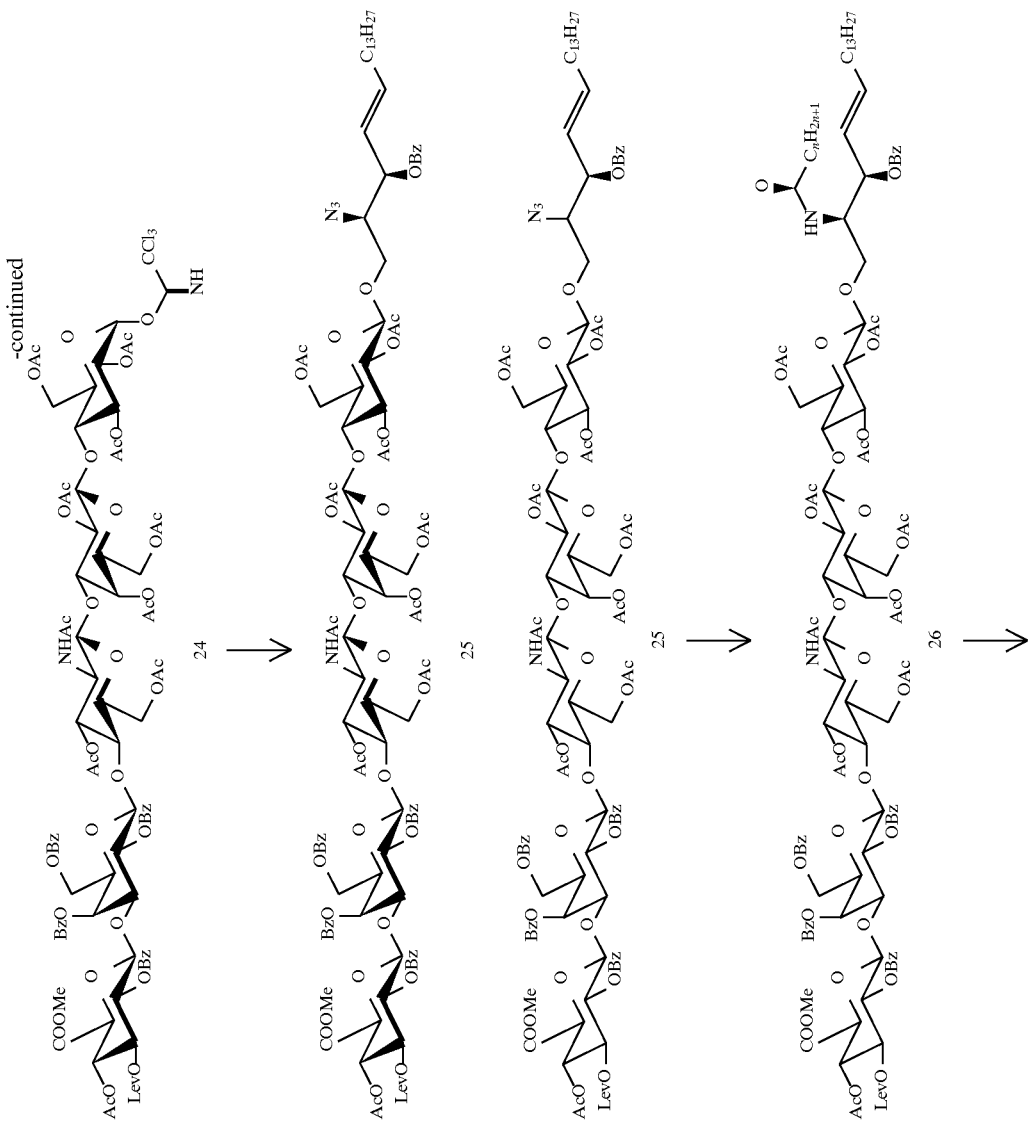

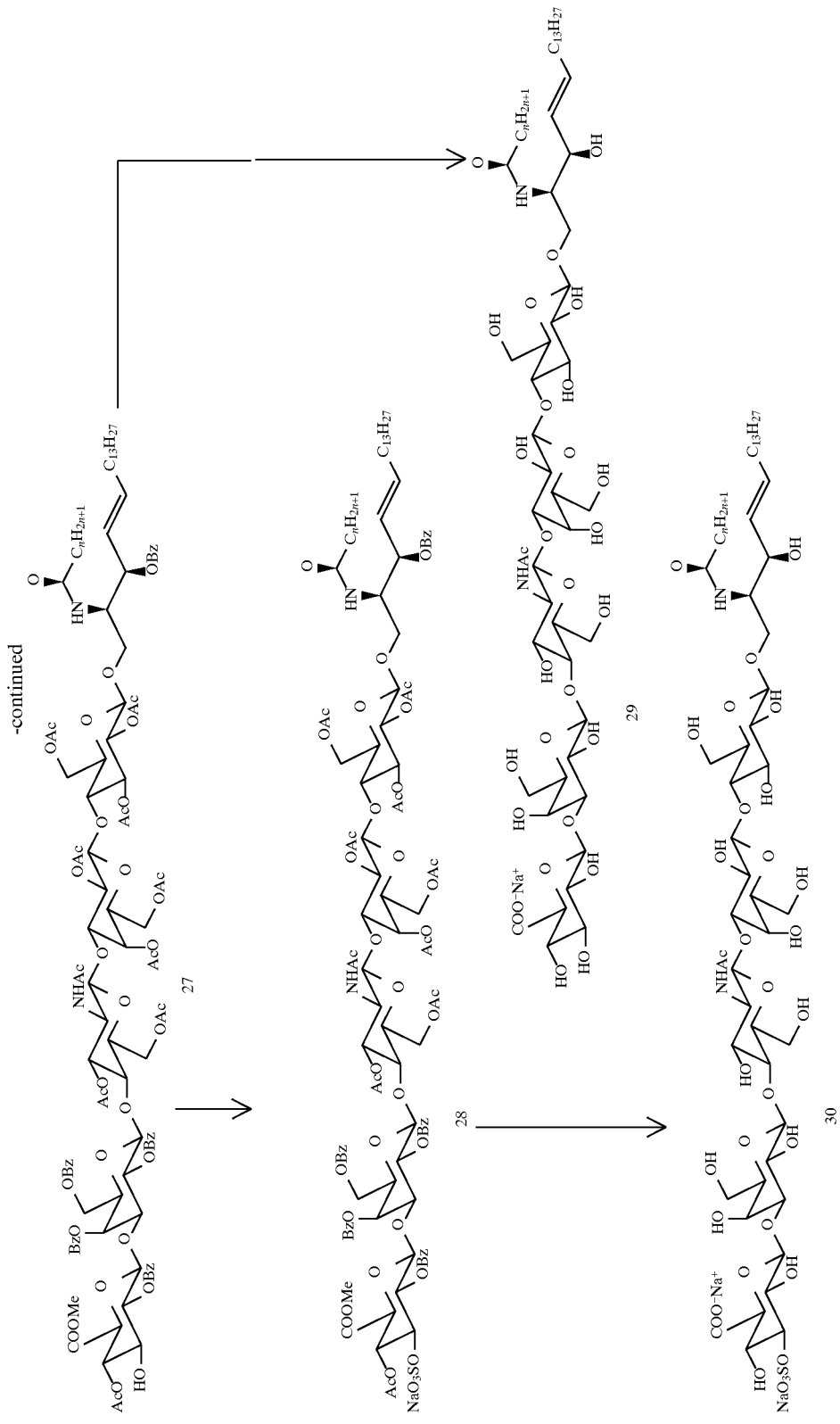

That is, the pentasaccharide compound 21 is obtained in as high as about 95% yield by the condensation of compound 13 and compound 20 in a solvent and in the presence of trimethyl silyl trifluoromethane sulfonate at a room temperature. This compound 21 is then subjected to a catalytic reduction to remove the benzyl protection group only, and then treated with acetic anhydride to convent the hydroxyl group to acetoxy group and obtain the compound 22. Thereafter, the endo trimethyl silyl ethyl oxy group is converted to hydroxy group by the reaction with trifluoroacetic acid and then to trichloroacetoimidoxy group to obtain compound 24.

To this compound 24, when azide sphingosine is used as an acceptor compound and condensed by using boron trifluoride etheride, compound 25 is obtained. Compound 26 having the desired end ceramide portion is obtained by the reaction of the compound 25 with octadecanoic acid or tetracosanoic acid and 1-ethyl-3-(3-dimethylaminopropyl-)carbodiimide hydrochloride in a solvent. Thus obtained compound 26 is, when reacted with hydrazine/acetic acid in ethanol at room temperatures, quantitaively converted to compound 27 having no protection group at 3-position of the eude glucuronic acid portion, from which the target compounds 29 and 30 are easy prepared in a higher yield.

That is, when compound 27 is subjected to a common treatment with LiOH and $CH_3ONa$, non-sulfated target compound 29 having free hydroxyl groups only can be easily obtained. When compound 27 is treated with sulfur trioxide-trimethylamine complex in a solvent, sulfation of 3-hydroxyl group of glucuronic acid portion is carried out almost quantitatively, thereby resulting compound 28 very easily and in a higher yield.

The subsequent treatment with LiOH and $CH_3ONa$, there obtains the sulfated target compound 30 in a higher yield.

Thus, in a glycolipid having an incorportated ceramic portion therein, when sulfation of 3-hydroxyl group is carried out after protecting 2-hydroxyl group of glucuronic portion with a benzoyl group and 4-hydroxyl group with an acetyl group, the said sulfation is proceeded almost quantitatively, and this is the most important finding of the present invention. In this sense, the compounds 26, 27 and 28 are the very important novel intermediate compounds for the synthesis of desired glycolipids.

The other target compounds 45 and 46, which are glycolipids each having 7 glycose segments, may be easily and advantageously prepared from the donar compound 36, which is tetra saccharide derived from the abovementioned donor compound 13, and acceptor compound 20 as follows.

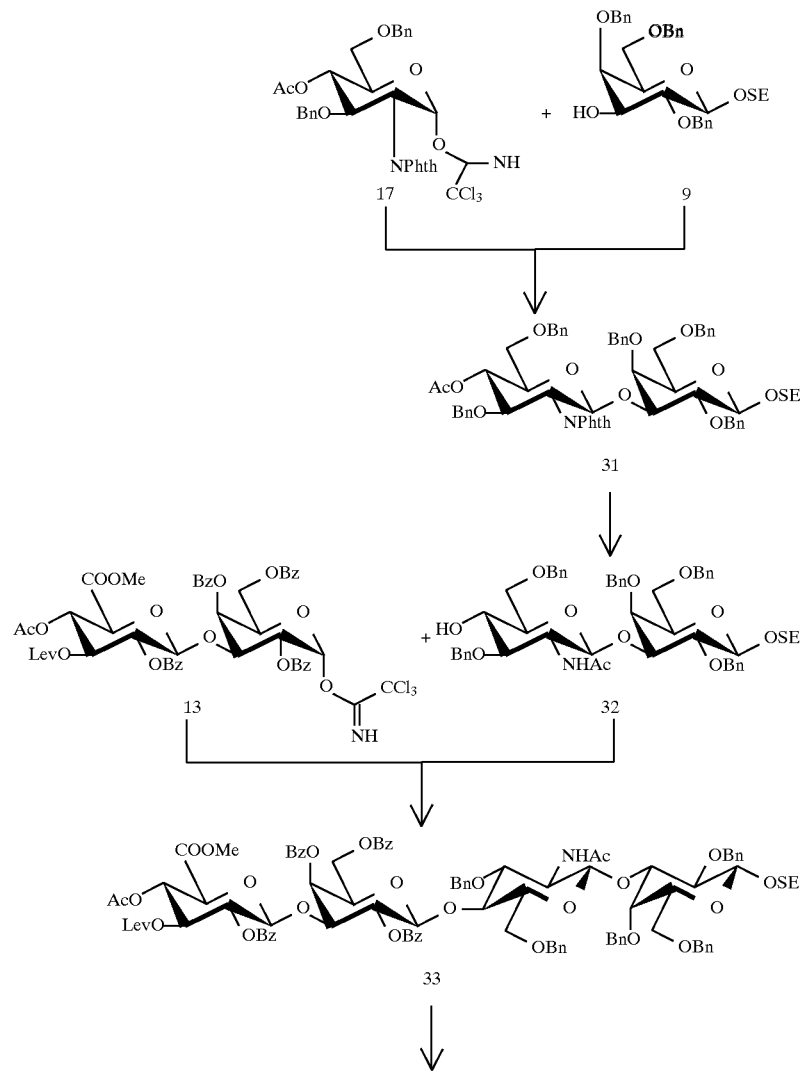

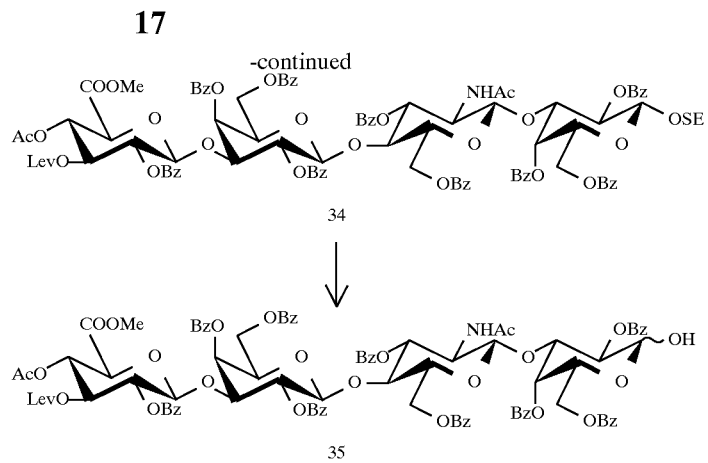

First, the donor compound 17, which is the glucosamine derivative derived from the abovementioned known compound 14, is reacted with a known compound of 2-(trimethyl silyl)ethyl-2,4,6-tri-O-benzyl-β-D-galactopyranoside(compound 9) in a solvent and in the presence of trimethyl silyl trifluoromethane sulfonate to obtain a disaccharide compound 31. From the latter, by the removal of acetyl group at the 4-position of glucosamine portion and concomitant conversion of 2-phthalimide group to acetylamino group, 2-(4-trimethyl silyl)ethyl-O-(2-acetamide-3,6-di-O-benzyl-2-deoxy-β-D-glucopyranosyl)-(1→3)-2,4,6-tri-O-benzyl-β-D-galactopyranoside(compound 32) is obtained.

Thus obtained compound 32 is used as acceptor compound and condensed with a donor compound 13 in a solvent and in the presence of trimethyl silyl trifluoromethane sulfonate at room temperature to obtain a tetrasaccharide compound 33 in as high as about 93% yield.

The latter is then derived to a tetrasaccharide donor compound 36 having an end trichloroacetoimidoxy group by using the same procedured as hereinbefore mentioned.

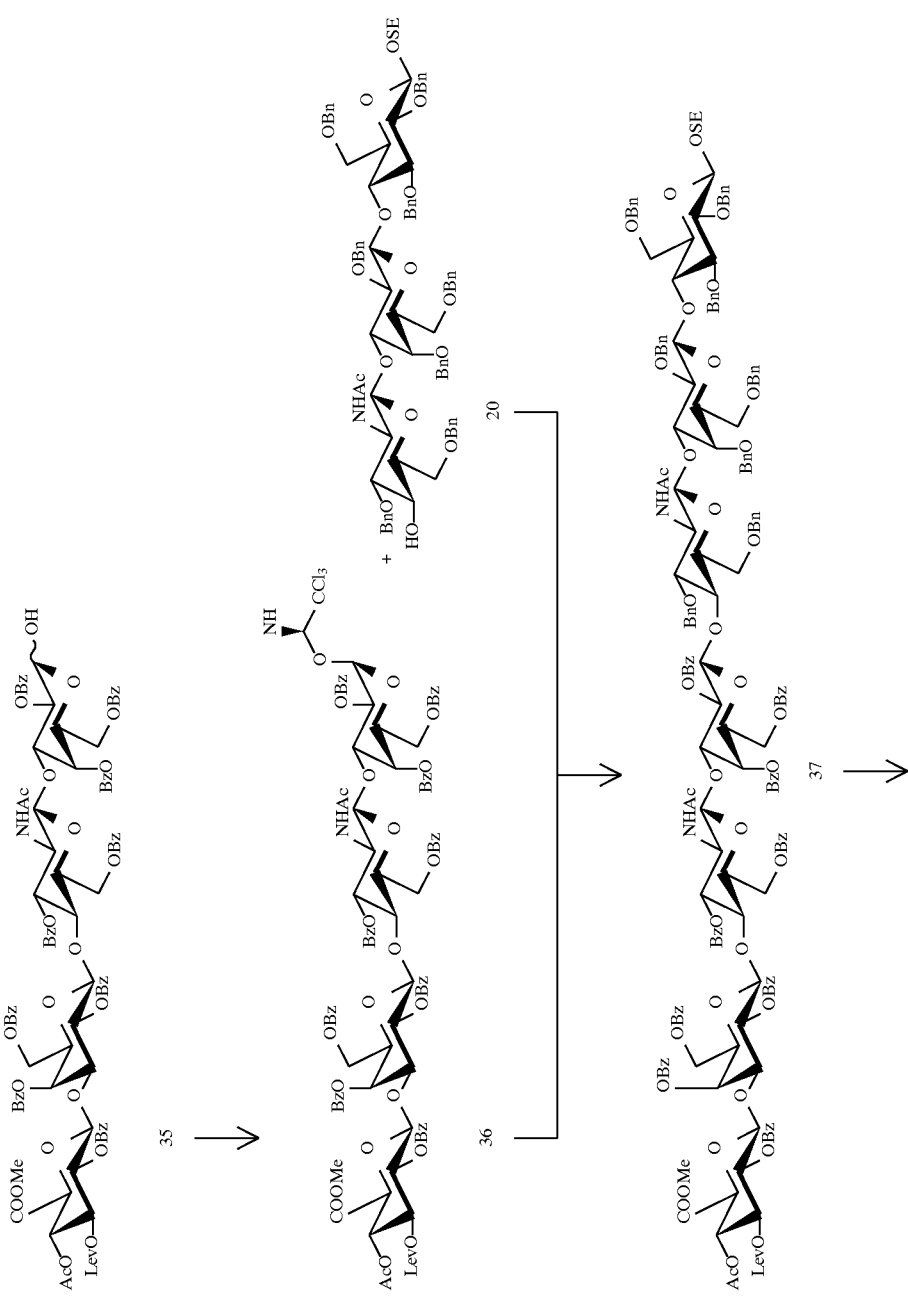

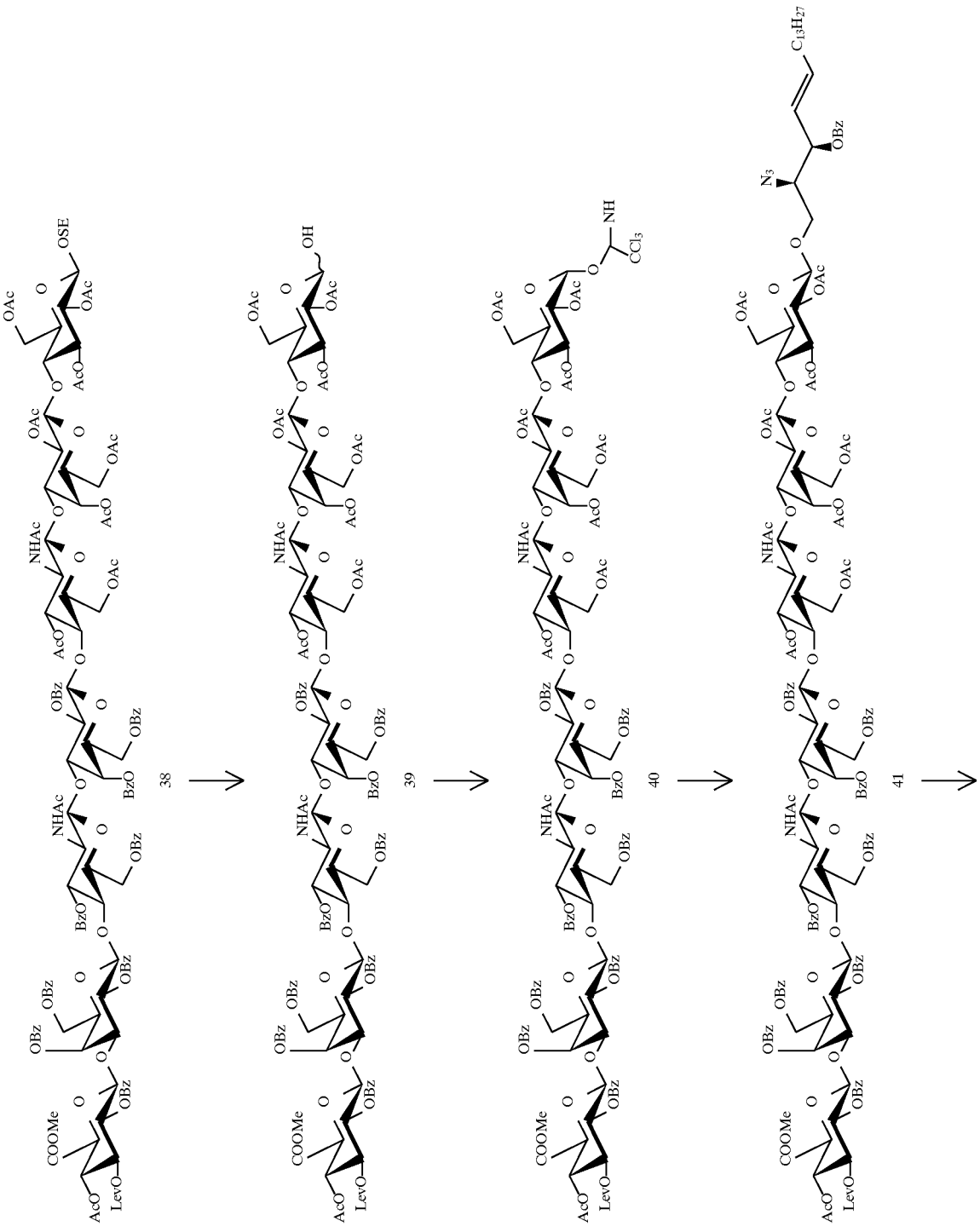

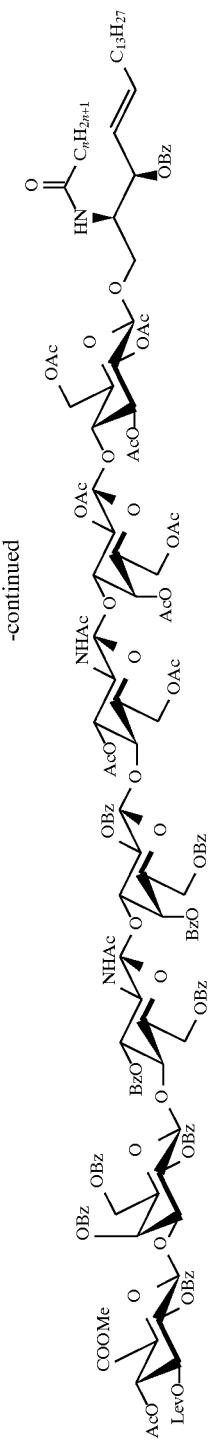
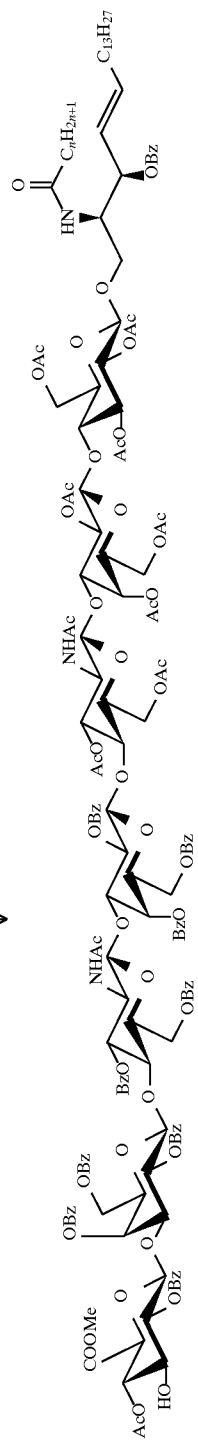
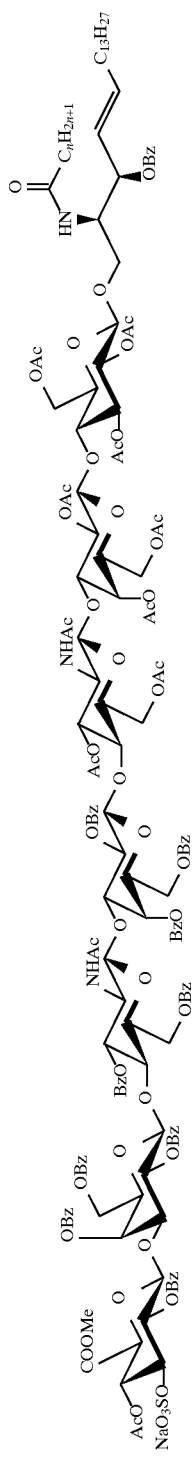

-continued
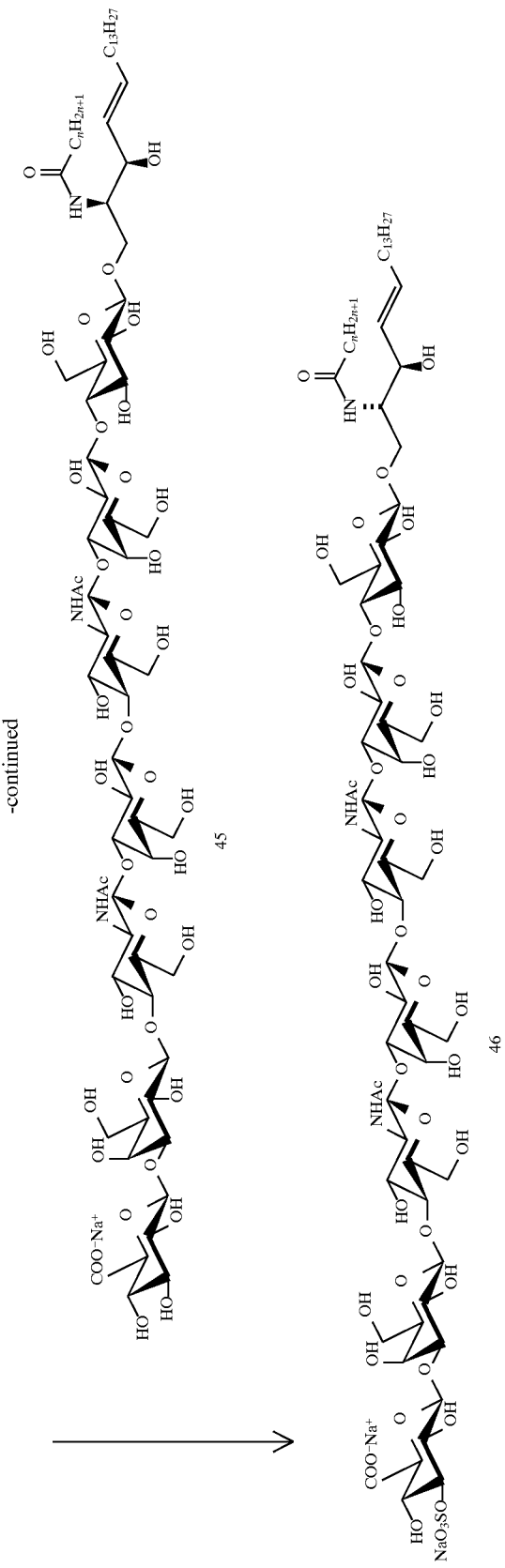

In the synthesis of the present target glycolipids having seven saccharose moiety (compounds 45 and 46), a hepta-saccharide compound 43 having a ceramide portion at an end and a glucuronic portion at the other end, whose 2 hydroxy group is protected with a benzoyl group, the 4-hydroxyl group with an acetyl group and the 3-hydroxyl group is free from an protection group, is first preparad from the tetra-saccharide donor compound 36 and the acceptor compound 20 herehinbefore stated, following the same procedures as hereinbefore stated in connection sith penta-saccharide glycolipids 29 and 30, and passing through compounds 37, 38, 39, 40, 41, and 42, from which a non-sulfated target compound 45 is directly obtained.

Or the compound 43 is treated with sulfur trioxide-trimethylamine complex in a solvent to obtain in a higher yield (for example 92% at 50° C.) a hepta-saccharide compound 44, i.e. a very important intermedeate compound for the synthesis of glycolipid, having a sulfated hydroxyl group at 3-position of the glucuronic acid portion, from which the target glycolopid having a hepta-saccharide moiety (compound 46) is easily obtained by removing the protection groups at the hydroxyl groups of saccharide portion.

Therefore, in the similar sense with the compounds 26, 27 and 28, the compounds 42, 43 and 44 are the important intermedeated for the synthesis of hepta-saccharide gly-colizids in the present invention.

The invention shall be now more fully explained in the following Examples.

In these examples, the following are known compounds as stated in the publications herein under mentioned.

Compound 1 . . . G. N. Bollenback, J. Am. Chem. Soc. 77, 3310~3315(1955)
Compound 9 . . . Akira Hasegawa et. al, J. Carbohydrate Chemistry 11(5)645~658(1992)
Compound 14. . . Akira Hasegawa et. al, J. Carbohydrate Reserch 200, 269~285(1990)
Compound 18 . . . Karl Janssen et. al J. Org. Chem. 53, 5629~5647(1988)

EXAMPLE 1

Synthesis of methyl [2-(trimethyl silyl)ethyl 2,3,4-tri-O-acetyl-β-D-glucopyranoside]uronate (compound 2)

To a solution of 2-(trimethyl silyl)ethanol (TMS ethanol) (24.0 g, 203.0 m mol) in dichloromethane (70 ml), were added silver carbonate (32.0 g, 116.0 m mol), silver perchlorate (25.5 g, 123.0 m mol) and powdered molecular sieves 4 Å (30 g), and the thus obtained mixture was stirred at room temperatures in a dark place for 10 hours. To this, methyl (tri-O-acetyl-α-D-glucopyranosyl bromide)-uronate (compound 1) (40.0 g, 100.1 m mol) was added at 10° C. and after vigorous stirring for 6 hours, the formed precipitates were collected, and washed with dichloromethane. After combining the filtrate and washing, it was concentrated and the concetration residue was subjected to column chromatography on silica gel (1200 g)(1:2 ethyl acetate: hexane elution) to obtain crystals of compound 2 (39.8 g, 91% yield). Recrystallization from ethyl acetate/hexane gave needles.

Elementary analysis as $C_{18}H_{30}O_{10}Si$ Calc. C 49.76 H 6.96 Found C 49.46 H 6.81

$[\alpha]_D$ –32.4° (c 0.5; $CHCl_3$)

M.P. 85.5°~87.5° C.

$^1$H-NMR($CDCl_3$) δ0.93 (m, 2H, $Me_3SiCH_2CH_2$)

2.01~2.03 (3 s, 9H, OAc)
3.55 (m, 1H, $Me_3SiCH_2CH_2$)
3.75 (s, 3H, COOMe)
4.03 (d, 1H, $J_{4,5}$=9.7 Hz, H-5)
4.56 (d, 1H, $J_{1,2}$=7.5 Hz, H-1)
4.99 (dd, 1H, $J_{2,3}$=9.3 Hz, H-2)
IR (KBr) 1760 and 1220(ester) 860 and 840 $cm^{-1}$ (TMS)

EXAMPLE 2

Synthesis of methyl [2-(trimethyl silyl)ethyl β-D-glucopyranosid]uronate (compound 3)

To a solution of compound 2 (39.8 g, 91.6 m mol) in methanol (200 ml), was added sodium methoxide (1.0 g), and the mixture was stirred at room temperatures for 2 hours. This mixture was treated with Amberlite 1R-120 (H⁺) resin, concentrated and the residue was subjected to column chromatography on silica gel (500 g)(3:1 ethyl acetate: hexane elution) to obtain compound 3 (26.5 g, 94% yield) as a syrup.

Elementary analysis as $C_{12}H_{24}O_7Si$ Calc. C 46.73 H 7.84 Found C 46.49 H 7.83

IR (KBr) 3500~3350 (OH)
1740 and 1220 (ester)
860 and 840 $cm^{-1}$ (TMS)

EXAMPLE 3

Synthesis of methyl [2-(trimethyl silyl)ethyl 4-O-acetyl-β-D-glucopyranosid]uronate (compound 4)

A suspension of compound 3 (26.5 g, 85.9 mmol) and di-n-butyl tin oxide (32.1 g, 129.0 m mol) in methanol (720 ml) was stirred and heated for 5 hs at 60° C., and then concentrated. To a solution of the concentrated residue in tetrahydrofuran (THF) (300 ml), was added triethylamine (11.3 g, 111.7 mmol) and heated at 45° C. Then, the mixture was added carefully with acetyl chloride (7.4 g, 94.3 m mol), stirred for 5 hrs at room temperature, and then concentrated. Column chromatography (2:1 ethyl acetate-hexane) of the residue on silica gel (1000g) gave compound 4 (18.2 g, 61% yield) and recovered compound 3 (5.5 g, 21%).

The compound 4 was recrystallized from ethylacetate-hexane:

Elementary analysis as $C_{14}H_{26}O_8Si_1$ Calc. C 47.98 H 7.48 Found C 47.87 H 7.33

M.P. 132.5°~134.0° C.

$[\alpha]_D$ –63.0° (c 0.8; $CHCl_3$)

$^1$H-NMR($CDCl_3$) δ 1.02 (m, 2H, $Me_3SiCH_2CH_2$)
2.10 (s, 3H, AcO)
3.73 (t, 1H, $J_{2,3}$=$J_{3,4}$=9.3 Hz,H-3)
3.74 (s, 3H, COOMe)
3.94 (d, 1H, H-5)
4.34 (d, 1H, $J_{1,2}$=7.7 Hz, H-1)
5.03 (t, 1H, $J_{4,5}$=9.3 Hz, H-4)
IR (KBr) 3490 (OH)
1760 and 1230 (ester)
860 and 840 $cm^{-1}$ (TMS)

EXAMPLE 4

Synthesis of methyl [2-(trimethyl silyl)ethyl 4-O-acetyl-2-O-benzyl-β-D-glucopyranosid]uronate (compound 5)

A suspension of compound 4 (18.0 g, 51.4 m mol) and di-n-butyltin Oxide (18.0 g, 72.3 m mol) in toluene (150 ml)

was stirred and heated for 1 h at 100° C. and then the mixture was added with a solution of benzoic anhydride (34.0 g, 150.3 m mol) in toluene (34 ml) at 100° C., and stirred for 5 min at 100° C. Then the mixture was concentrated. Columnn chromatography (1:1 ethyl acetate-hexane) of the residue on silica gel (700 g) gave compound 5 (14.0 g, 60% yield), and recovered compound 4 (1.8 g, 10%). The compound 5 was recrystallized from ethylacetate-hexane:

Elementary analysis as $C_{21}H_{30}O_9Si_1$ Calc. C 55.49 H 6.65 Found C 55.31 H 6.62

M.P. 119.0°~121.0° C.

$[\alpha]_D$ –33.9° (c 0.9; $CHCl_3$)

$^1$H-NMR($CDCl_3$) δ 0.91 (m, 2H, $Me_3SiCH_2CH_2$)
2.10 (s, 3H, AcO)
3.58 (m, 1H, $Me_3SiCH_2CH_2$)
3.78 (s, 3H, COOMe)
4.05 (d, 1H, H-5)
4.70 (d, 1H, $J_{1,2}$=7.2 Hz, H-1)
5.11 (dd, 1H, $J_{2,3}$=9.3 Hz, H-2)
5.22 (t, 1H, $J_{3,4}$=$J_{4,5}$=9.3 Hz, H-4)
7.42–8.07 (m, 5H, 1 Ph)
IR (KBr) 3480 (OH)
1750,1730,1270 and 1250 (ester)
860 and 840 (TMS)
770 and 710 cm$^{-1}$ (Ph)

EXAMPLE 5

Synthesis of methyl [2-(trimethyl silyl)ethyl 4-O-acetyl-2-O-benzoyl-3-O-levulinoyl-β-D-glucopyranosid)uronate (compound 6)

To a solution of levulinic anhydride (24.0 g, 112.0 m mol) in pyridine (70 ml), were added compound 5 (10.0 g, 22.0 m mol), and 4-dimethyl amino pyridine (DMAP)(1.3 g, 106.4 m mol). Then, the mixture was stirred over night at room temperature and concentrated. Column chromatography (3:2 ethyl acetate-hexane) of the residue on silica gel (500 g) gave compound 6 (9.2 g, 76% yield) as needles:

Elementary analysis as $C_{26}H_{36}O_{11}Si_1$ Calc. C 56.51 H 6.57 Found C 56.22 H 6.43

M.P. 89.5°~91.0° C.

$[\alpha]_D$+11.8° (c 1.0; $CHCl_3$) $^1$H-NMR($CDCl_3$) δ 0.88 (m, 2H, $Me_3SiCH_2CH_2$)
2.04 (s, 3H, Ac of Lev or OAc)
2.08 (s, 3H, Ac of Lev or OAc)
2.40 (m, 4H, $CH_2CH_2Ac$)
3.56 (m, 1H, $Me_3SiCH_2CH_2$)
3.78 (s, 3H, COOMe)
4.01 (m, 1H, $Me_3SiCH_2CH_2$)
4.11 (d, 1H, $J_{4,5}$=9.6 Hz,H-5)
4.70 (d, 1H, $J_{1,2}$=7.2 Hz, H-1)
5.26 (dd, 1H, H-2)
5.30 (t, 1H, H-4)
5.46 (t, 1H, $J_{2,3}$=$J_{3,4}$=9.6 Hz,H-3)
7.41–8.00 (m, 5H, 1 Ph)
IR (KBr) 1750,1720,1270 and 1240 (ester)
860 and 840 (TMS)
770 and 720 cm$^{-1}$ (Ph)

EXAMPLE 6

Synthesis of methyl (4-O-acetyl-2-O-benzoyl-3-O-levulinoyl-D-glucopyranoside)uronate (compound 7)

To a solution of compound 6 (9.0 g, 16.3 m mol) in dichloromethane(50 ml), was added trifluoro acetic acid (20 ml) at 0° C., and the mixture was stirred for 2 hrs at room temperature and concentrated.

Column chromatograph (2:1 ethyl acetate-hexane) of the residue on silica gel (200 g) gave compound 7 (7.3 g, quantitative yield) as an amorphous mass:

Elementary analysis as $C_{21}H_{24}O_{11}$ Calc. C 55.75 H 5.35 Found C 55.66 H 5.25

$[\alpha]_D$+113.1° (c 1.2; $CHCl_3$)

IR (KBr) 3440 (OH) 1750,1720,1260 and 1230 cm$^{-1}$ (ester)

EXAMPLE 7

Synthesis of methyl (4-O-acetyl-2-O-benzoyl-3-O-levulinoyl-α-D-glucopyranosyl trichloroacetimidate) uronate (compound 8)

To a solution of compound 7 (5.0 g, 11.1 m mol) in dichloromethane (50 ml ) and trichloroacetonitrile (11 ml), was added 1,8-diazabicyclo[5.4.0]undec-7-ene (DBU, 0.30 g) at 0° C., and the mixture was stirred for 2 hrs at 0° C. and directly eluted from a column of silica gel (300 g) with ethylacetate-hexane (1:1) to give compound 8 (6.2 g, 95% yield) as an amorphous mass:

Elementary analysis as $C_{23}H_{24}N_1O_{11}Cl_3$ Calc. C 46.29 H 4.05 N 2.35 Found C 46.02 H 3.97 N 2.15

$[\alpha]_D$+103.9° (c 0.7; $CHCl_3$)

$^1$H-NMR($CDCl_3$) δ 2.07 (s, 3H, Ac of Lev or OAc)
2.14 (s, 3H, Ac of Lev or OAc)
2.56 (m, 4H, $CH_2CH_2Ac$)
3.70 (s, 3H, COOMe)
4.55 (d, 1H, $J_{4,5}$=10.2 Hz,H-5)
5.87 (t, 1H, $J_{2,3}$=$J_{3,4}$=10.2 Hz, H-3)
6.78 (d, 1H, $J_{1,2}$=3.5 Hz, H-1)
7.39–7.99(m, 5H, 1 Ph)
8.64 (s, 1H, C=NH)
IR (KBr) 3320 (NH)
1760,1730,1270 and 1220 (ester)
760 and 710 cm$^{-1}$ (Ph)

EXAMPLE 8

Synthesis of 2-(trimethyl silyl)ethyl O-(methyl 4-O-acetyl-2-O-benzoyl-3-O-levulinoyl-β-D-glucopyranosyluronate)-(1→3)-2,4,6-tri-O-benzyl-β-D-galactopyranoside (compound 10)

To a solution of compound 8 (2.3 g, 3.85 m mol) in dichloromethane (10 ml), were added 2-(trimethyl silyl) ethyl 2,4,6-tri-O-benzyl-β-D-galactopyranoside (compound 9, 3.5 g, 6.35 m mol), and powdered molecular sieves 4 Å (3.0 g), and the mixture was stirred for 5 hrs. at room temperature (mixture A).

A solution of trimethyl silyl trifluoromethane sulfonate (TMSOTf) (0.85 g, 3.82 m mol) in dichloromethane (1 ml) was treated with powdered molecular sieres 4 Å (1.0 g) as above-mentioned and then added to mixture A at 0° C. After stirring for 1 hr, the mixture was neutralized with triethylamin and filtered. The residue was washed with dichloromethane and the combined filtrate and washing was concentrated. Column chromatography (1:2 ethyl acetate-hexane) of the residue on silica gel (100 g) afforded compound 10 (3.6 g, 95% yield based on compound 8) as an amorphous mass:

Elementary analysis as $C_{53}H_{64}O_{16}Si_1$ Calc. C 64.62 H 6.55 Found C 64.59 H 6.42

$[\alpha]_D$ –0.6° (c0.7; $CHCl_3$) $^1$H-NMR($CDCl_3$) δ 0.92 (m, 2H,$Me_3SiCH_2CH_2$)

2.03 (s, 3H, Ac of Lev or OAc)
2.09 (s, 3H, Ac of Lev or OAc)
2.46 (m, 4H, CH$_2$CH$_2$Ac)
3.72 (s, 3H, COOMe)
3.85 (dd, 1H, J$_{2,3}$=9.7, J$_{3,4}$3.0 Hz, H-3 for Gal)
3.94 (d, 1H, H-4 for Gal)
3,98 (d, 1H, J$_{4,5}$=9.8 Hz H-5 for Glc A)
4.28 (d, 1H, J$_{1,2}$=7.5 Hz, H-1 for Gal)
5.23 (d, 1H, J$_{1,2}$=7.7 Hz, H-1 for GlcA)
5.31 (t, 1H, J$_{3,4}$=9.8 Hz H-4 for Glc A)
7.19–7.90(m, 20H, 4 Ph)
IR (KBr) 1760,1720,1270 and 1230 (ester)
860 and 840 (TMS)
770, 740, 710 cm$^{-1}$ (Ph)

EXAMPLE 9

Synthesis of 2-(trimethyl silyl)ethyl O-(methyl 4-O-acetyl-2-O-benzoyl-3-O-levulinoyl-β-D-glucopyranosyl uronate)-(1→3)-2,4,6-tri-O-benzyl-β-D-galactopyranoside (compound 11)

A solution of compound 10 (9.5 g, 9.64 m mol) in methanol (100 ml) and ethyl acetate (50 ml) was hydrogenolyzed in the presence of 10% Pd-C (3.0 g) for 24 hrs at room temperature, then filtrated and concentrated. The residue was benzoylated with benzoyl chloride (5.1 g, 36.3 m mol)-pyridine (30 ml) for one night at room temperature. The product was purified by chromatography on a column of silica gel (500 g), eluted with 1:1 ethyl acetate-hexane and afforded compound 11 (8.1 g, 82% yield) as crystals.

Elementary analysis as C$_{53}$H$_{58}$O$_{19}$Si$_1$ Calc. C 61.98 H 5.69 Found C 61.69 H 5.46

M.P. 118.5°~120.5° C.

$[\alpha]_D$+36.2° (c 0.4 ; CHCl$_3$)
$^1$H-NMR(CDCl$_3$) δ 6 0.79 (m, 2H,Me$_3$SiCH$_2$CH$_2$)
1.97 (s, 3H, Ac of Lev or OAc)
2.02 (s, 3H, Ac of Lev or OAc)
2.31 (m, 4H, CH$_2$CH$_2$Ac)
3.68 (s, 3H, COOMe)
4.02 (d, 1H, J$_{4,5}$=9.8 Hz, H-5 for Glc A)
4.28 (dd, 1H, J$_{2,3}$=10.0, J$_{3,4}$=3.4 Hz, H-3 for Gal)
4.61 (d, 1H, J$_{1,2}$=7.9 Hz, H-1 for Gal),
4.88 (d, 1H, J$_{1,2}$=7.3 Hz, H-1 for Glc A)
5.06 (dd, 1H, J$_{2,3}$=9.2 Hz, H-2 for GlcA)
5.56 (dd, 1H, H-2 for Gal )
5.85 (d, 1H, H-4 for Gal)
7.17–8.11(m, 20H, 4 Ph)
IR (KBr) 1730,1270 (ester)
860,840 (TMS)
770, 710 cm$^{-1}$ (Ph)

EXAMPLE 10

Synthesis of O-(methyl 4-O-acetyl-2-O-benzoyl-3-O-levulinoyl-β-D-glucopyranosyl uronate)-(1→3)-2,4,6-tri-O-benzoyl-D-galactopyranose (compound 12)

To a solution of compound 11 (5.1 g, 4.97 m mol) in dichloromethane (60 ml), was added trifluoro acetic acid (10 ml) at 0° C., and the mixture was stirred for 2 hrs at room temperature and concentrated. Column chromatography (1:1 ethyl acetate-hexane) of the residue on silica gel (200 g) gave compound 12 (4.6 g, quantitative yield) as an amorphous mass:

Elementary analysis as C$_{48}$H$_{46}$O$_{19}$ Calc. C 62.20 H 5.00 Found C 61.97 H 4.74

$[\alpha]_D$+72.0° (c 0.5 ; CHCl$_3$)
IR (KBr) 3480 (OH)
1730,1270 (ester)
710, 690 cm$^{-1}$ (Ph)

EXAMPLE 11

Synthesis of O-(methyl 4-O-acetyl-2-O-benzoyl-3-O-levulinoyl-β-D-glucopyranosyl uronate)-(1→3)-2,4,6-tri-O-benzoyl-α-D-galactopyranosyl trichloroacetimide (compound 13)

To a solution of compound 12 (2.5 g, 3.13 m mol) in dichloromethane (30 ml) and trichloroacetonitrile (5 ml), was added 1,8-diazabicyclo [5.4.0]undec-7-ene (DBU, 50 mg) at 0° C., and the mixture was stirred for 2 hrs at 0° C. and directly eluted from a column of silica gel (100 g) with ethyl acetate-hexane (2:3) to give compound 13 (2.7 g, 93% yield) as an amorphous mass:

Elementary analysis as C$_{50}$H$_{46}$N$_1$O$_{19}$Cl$_3$ Calc. C 56.06 H 4.33 N 1.31 Found C 56.03 H 4.07 N 1.02

$[\alpha]_D$+79.0° (c 0.9 ; CHCl$_3$)
$^1$H-NMR(CDCl$_3$) δ 1.98 (s, 3H, Ac of Lev or OAc)
2.05 (s, 3H, Ac of Lev or OAc)
2.32 (m, 41H, CH$_2$CH$_2$Ac)
3.75 (s, 3H, COOMe)
4.15 (d, 1H, J$_{4,5}$=9.2 Hz, H-5 for Glc A)
5.03 (d, 1H, J$_{1,2}$=7.0 Hz, H-1 for Glc A)
5.71 (dd, 1H,J$_{2,3}$=10.2 Hz. H-2 for Gal)
6.02 (d, 1H, J$_{3,4}$=3.1 Hz, H-4 for Gal)
6.73 (d, 1H, J$_{1,2}$=3.7 Hz, H-1 for Glc A)
7.09–8.10(m, 20H, 4 Ph) 8.47 (s, 1H, C═NH)
IR (KBr) 3340 (NH)
1730,1270 (ester)
760, 710 , 690 cm$^{-1}$ (Ph)

EXAMPLE 12

Synthesis of 2-(trimethyl silyl)ethyl 4-O-acetyl-3,6-di-O-benzyl-2-deoxy-2-phthalimido-β-D-glucopyranoside (compound 15)

To a solution of 2-(trimethyl silyl)ethyl 3,6-di-O-benzyl-2-deoxy-2-phthalimido-β-D-glucopyranoside (compound 14, 8.0 g, 13.6 m mol) in pyridine (40 ml), was added acetic anhydride (10 ml) at 0° C., and the mixture was stirred for 5 hrs at room temperature, and concentrated. Column chromatography (1:2 ethyl acetate-hoxane) of the residue on silica gel (200 g) gave compound 15 (8.6 g, quantitative yield) as crystals:

Elementary analysis as C$_{35}$H$_{41}$N$_1$O$_8$Si$_1$Calc. C 66.54 H 6.54 N 2.22 Found C 66.48 H 6.30 N 2.04

M.P. 87.5°~89.0° C.

$[\alpha]_D$+54.2° (c 0.7 ; CHCl$_3$)
$^1$H-NMR(CDCl$_3$) δ 0.77 (m, 2H, Me$_3$SiCH$_2$CH$_2$)
1.95 (s, 3H, AcO)
4.24 (d, 1H, J$_{1,2}$=8.3 Hz,J$_{2,3}$=10.8 Hz,H-2)
4.42 (dd, 1H,J$_{3,4}$=9.0 Hz. H-3 )
5.14 (dd, 1H, J$_{4,5}$=9.7 Hz, H-4 )
5.17 (d, 1H, H-1 )
6.87–7.68(m, 14H, 2 Ph, phthaloyl-H)
IR (KBr) 1750,1230 (ester)
1720 (imide)
860, 840 (TMS)
740, 720 , 700 cm$^{-1}$ (Ph)

EXAMPLE 13

Synthesis of 4-O-acetyl-3,6-di-O-benzyl-2-deoxy-2-phthalimido-D-glacopyranose (compound 16)

To a solution of compound 15 (8.5 g, 13.5 m mol) in dichloromethane (80 ml), was added trifluoroacetic acid (15 ml) at 0° C., and the mixture was stirred for 2 hrs at room temperature and concentrated. Column chromatography (1:1 ethyl acetate-hexane) of the residue on silica gel (200 g) gave compound 16 (7.1 g, quantitative yield) as a syrup:

Elementary analysis as $C_{30}H_{29}N_1O_8$ Calc. C 67.79 H 5.50 N 2.64 Found C 67.70 11 5.21 N 2.36

$[\alpha]_D +64.9°$ (c 0.5; $CHCl_3$)
IR (KBr) 3470 (OH)
1750,1230 (ester)
1720 (imide)
740, 720 , 700 $cm^{-1}$ (Ph)

EXAMPLE 14

Synthesis of 4-O-acetyl-3,6-di-O-benzyl-2-deoxy-2-phthalimido-α-D-glucopyranosyl trichloroacetimidate (compound 17)

To a solution of compound 16 (6.9 g, 13.0 m mol) in dichloromethane (70 ml) and trichloroacetonitrile (12 ml), was added 1,8-diazabicyclo [5. 4.0]undec-7-ene (DBU, 0.2 g) at 0° C., and the mixture was stirred for 1 h at 0° C. and directly subjected to a column chromatograpy with silica gel (200 g) using, ethyl acetate-hexane (1:1) as an eluent to give amorphous compound 17 (7.9 g, 90%):

Elementary analysis as $C_{32}H_{29}N_2O_8Cl_3$ Calc. C 56.86 H 4.32 N 4.14 Found C 56.76 H 4.28 N 4.01

$^1$H-NMR($CDCl_3$) δ 1.95 (s, 3H, AcO)
4.14 (dd, 1H, H-3)
5.25 (m , 1H, H-4)
6.43 (d, 1H, H-1 )
8.59 (s, 1H, C=NH)
IR (KBr) 3340 (NH)
1750,1230 (ester)
1720 (imide)
740, 720, 700 $cm^{-1}$ (Ph)

EXAMPLE 15

Synthesis of 2-(trimethyl silyl)ethyl O-(4-O-acetyl-3,6-di-O-benzyl-2-deoxy-2-phthalimido-β-D-glucopyranosyl)-(1→3)-O-(2,4,6-tri-O-benzyl-β-D-galactopyranosyl)-(1→3)-2,3,6-tri-O-benzyl-β-D-glucopyranoside (compound 19)

To a solution of compound 17 (5.0 g, 7.40 m mol) in dichloromethane (20 ml ), were added 2-(trimethyl silyl) ethyl O-(2,4,6-tri-O-benzyl-β-D-galactopyranosyl)-(1→4)-2,3,6-tri-O benzyl-β-D-glucopyranoside (compound 18, 14.5 g, 14.7 m mol), and powdered molecular sieves 4 Å (5.0 g), and the mixture was stirred for 5 hrs at room temperature (mixture A). A solution of trimethylsilyl trifluoromethane sulfonate (TMSOTf) (0.5 g, 2.25 m mol) in dichloromethane (1 ml) was treated with powdered molecular sieves 4 Å (0.6 g) as above-mentioned, and then added to mixture A at −5° C. After stirred for 1 h at 10° C., the mixture was neutralized with trietylamine and filtered, and the residue was washed with dichlorometane. The combined filtrate and washings were concentrated and the residue was subjected to a column chromatography with silica gel(500 g) using ethyl acetate and hexane (1:2)as an eluent, to obtain 10.3 g (93% yield based on compound 17) of compound 19 (as a syrup).

Elementary analysis as $C_{89}H_{97}N_1O_{18}Si_1$ Calc. C 71.42 H 6.53 N 0.96 Found C 71.35 H 6.44 N 0.75

$[\alpha]_D +7.4°$ (c 0.8; $CHCl_3$)
$^1$H-NMR($CDCl_3$) δ 0.97 (m, 2H,$Me_3SiCH_2CH_2$)
1.96(s, 3H, AcO)
5.12 (dd, 1H, H-4 for Glc N)
5.38 (d, 1H, $J_{1,2}$=8.4 Hz, H-1 for Glc N)
6.88–7.28(m, 44H, 8 Ph, phthaloyl-H)
IR (film) 1770,1270 (ester)
1720 (imide)
740, 720 , 700 $cm^{-1}$ (Ph)

EXAMPLE 16

Synthesis of 2-(trimethyl silyl)ethyl O-(2-acetamido-3,6-di-O-benzyl-2-deoxy-β-D-glucopyranosyl-(1→3)-O-(2,4,6-tri-O-benzyl-β-D-galactopyranosyl)-(1→4)-2,3,6-tri-O-benzyl-β-D-glucopyranoside (compound 20)

A solution of compound 19 (10.0 g, 6.7 m mol) in methanol (150 ml) was stirred with sodium methoxide (300 mg) for 3 hrs at room temperature. The mixture was treated with Amberlite IR-120($H^{30}$ )resin and concentrated, and a solution of the thus obtained residue in aqueous 95% ethanol (80 ml) was heated for 4 hrs under reflux. The precipitate was collected and washed with ethanol, and the combined filtrate and washings were concentrated. The residue was treated with acetic anhydride (5 ml) in methanol (80 ml) for 1 h at room temperature, pyridine (10 ml) was added to the mixture, and the mixture was concentrated. Thus obtained residue was dissolved in dichloro methane (300 ml) and the solution was successively washed with 2M hydrochloric acid, water, and M sodium corbonate, and then dried ($Na_2SO_4$) and concentrated. Column chromatography (2:3 ethyl acetate-hexane) of the residue on silica gel (400 g) afforded compound 20 (7.7 g, yield 84%) as a syrup.

Elementary analysis as $C_{81}H_{95}N_1O_{16}Si_1$ Calc. C 71.18 H 7.01 N 1.02 Found C 70.97 H 6.96 N 0.83

$[\alpha]_D −6.8°$ (c 1.2; $CHCl_3$) $^1$H-NMR($CDCl_3$) δ 1.02 (m, 2H,$Me_3SiCH_2CH_2$)
1.47 (s, 3H, AcN)
7.12–7.33 (m, 40H, 8 Ph)
IR (film) 3410 (OH and NH)
1640,1540 (amide)
860, 840 (TMS)
740, 700 $cm^{-1}$ (Ph)

EXAMPLE 17

Synthesis of 2-(trimethyl silyl)ethyl O-(methyl 4-O-acetyl-2-O-benzoyl-3-0-levulinoyl-β-D-glucopyranosyluronate)-(1→3)-O-(2,4,6-tri-O-benzoyl-β-D-galactopyranosyl)-(1→4)-O-(2-acetamido-3,6-di-O-benzyl-2-deoxy-β-D-glucopyranosyl)-(1→3)-O-(2,4,6-tri-O-benzyl-β-D-galactopyranosyl)-(1→4)-2,3,6-tri-O-benzyl-β-D-glucopyranoside (compound 21)

To a solution of compound 13 (2.4 g, 2.24 m mol) in dichloromethane (12 ml), were added compound 20 (6.0 g, 4.40 m mol), and powdered molecular sieves 4 Å (2.5 g), and the mixture was stirred for 5 hrs at room temperature (mixture A).

A solution of TMSOTf (75 mg, 0.34 m mol) in dichloromethane (1 ml) was treated with powdered molecular sieves 4 Å (0.5 g) as abovementioned, and then added to mixture A at room temperature. After stirring for one night at room temperature, the mixture was neutralized with triethyl amie and filtered, the collected was washed with dichloromethane and the washing and the abovementioned filtrate were combined, concentrated and the concentrateion residue was subjected to a column chromatography with silica gel (300 g), by using as an eluent 1:1 ethyl acetate: hexane, to obtain 4.8 g of compound 21 (yield 94% based on compound 13) and recover 2.8 g (47%) of compound 20.

Elementary analysis as $C_{129}H_{139}N_1O_{34}Si_1$ Calc. C 68.09 H 6.16 N 0.62 Found C 67.86 11 6.04 N 0.54

$[\alpha]_D$+3.2° (c 0.4 ; CHCl$_3$)
$^1$H-NMR(CDCl$_3$) δ 1.01 (m, 2H,Me$_3$SiCH$_2$CH$_2$)
1.67 (s, 3H, AcN)
1.97 (s, 3H, AcO or Ac of Lev)
2.04 (s, 3H, AcO or Ac of Lev))
2.32 (m, 1H, CH$_2$CH$_2$Ac)
3.70 (s, 3H, COOMe)
7.01–8.06 (m, 60H, 12 Ph)
IR (film) 3400 (NH)
1730, 1270 (ester)
1680, 1590 (amide)
740, 710, 700 cm$^{-1}$(Ph)

EXAMPLE 18

Synthesis of 2-(trimethyl silyl)ethyl O-(methyl 4-O-acetyl-2-O-benzyl-3-O-levulinoyl-β-D-glucopyranosyluronate-(1→3)-O-(2,4,6-tri-O-benzyl-β-D-galactopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl)-(1→4)-2,3,6-tri-O-acetyl-β-D-glucopyranoside (compound 22)

A solution of compound 21 (4.5 g, 2.0 m mol) in methanol (50 ml) and ethyl acetate (20 ml) was hydrogenolyzed in the presence of 10% Pd-C (2.0 g) for 30 hrs at room temperature, then filtered and concentrated. The residue was acetylated with acetic anhydride (20 ml )-pyridine (40 ml) for 20 hrs at room temperature and concentrated. The product was purified by chromatography on a column of silica gel (350 g) with (4:1) ethyl acetate-hexane afforded compound 22 (3.7 g, quantitative yield) as needles:

Elementary analysis as $C_{89}H_{107}N_1O_{42}Si_1$ Calc. C 56.53 H 5.70 N 0.74 Found C 56.50 H 5.52 N 0.70

$[\alpha]_D$+12.5° (c 0.5; CHCl$_3$)
$^1$H-NMR(CDCl$_3$) δ 0.88 (m, 2H,Me$_3$SiCH$_2$CH$_2$)
1.77 (s, 3H, AcN)
1.84–2.09(10 s, 30H,9 AcO, Ac of Lev)
2.33 (m, 411, CH$_2$CH$_2$Ac)
3.71 (s, 3H, COOMe)
4.27 ,4.45, 4.51 (3d,3H, J$_{1,2}$=7.9 Hz, H-1a or 1b or 1d)
4.64 (d,1H, J$_{1,2}$=7.9 Hz, H-1c)
4.82 (d,1H, J$_{1,2}$=7.3 Hz, H-1e)
5.50 (dd,1H, J$_{2,3}$=10.0 Hz, H-2d)
5.86 (d, 1H, J$_{3,4}$=3.2 Hz, H-4d)
7.15–8.10 (m, 20H, 4 Ph)
IR (film) 3390 (NH)
1750,1230 cm$^{-1}$ (ester)

EXAMPLE 19

Synthesis of O-(methyl 4-O-acetyl-2-O-benzoyl-3-O-levulinoyl-β-D-glucopyranosyluronate)-(1→3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3)-O-2,4,6-tri-O-acetyl-β-D-galactopyranosyl-(1→4)-2,3,6-tri-O-acetyl-β-D-glucopyranose (compound 23)

To a solution of compound 22 (3.3 g, 1.74 m mol) in dichloromethane (25 ml), was added trifluoro acetic acid (8 ml) at 0° C., and the mixture was stirred for 1.5 hrs at room temperature, and concentrated. Column chromatography (ethyl acetate only) of the residue on silica gel (200 g) gave compound 23 (3.0 g, 96% yield) as a syrup:

Elementary analysis as $C_{84}H_{95}N_1O_{42}$ Calc. C 56.34 H 5.35 N 0.78 Found C 56.10 H 5.13 N 0.70

$[\alpha]_D$+31.6° (c 0.4; CHCl$_3$)
IR (film) 3380 (OH,NH)
1750,1230 cm$^{-1}$ (ester)

EXAMPLE 20

Synthesis of O-(methyl 4-O-acetyl-2-O-benzoyl-3-O-levulinoyl-β-D-glucopyranosyluronate -(1→3)-O-(2,4,6-tri-O-benzoyl-β-D-galactopyranosyl)-(1→4)-O-(2-acetamido-3,6-di-O-acetyl-2-deoxy-β-D-glucopyranosy)-(1→3)-O-(2,4,6-tri-O-acetyl-β-D-galactopyranosyl)-(1→4)-2,3,6-tri-O-acetyl-β-D-glucopyranosyl trichloroacetimidate (compound 24)

To a solution of compound 23 (1.5 g, 0.85 m mol) in dichloromethane (30 ml) and trichloroacetonitrile (3 ml), was added 1,8-diazabicyclo[5.4.0]undec-7-ene (DBU, 25 mg) at –10 ° C., and the mixture was stirred for 4 hrs at 0° C. and directly eluted from a column of silica gel (300 g) with ethyl acetate-hexane (4:1) to give amorphous compound 24 (1.5 g, 94% yield):

Elementary analysis as $C_{86}H_{95}N_2O_{42}Cl_3$ Calc. C 53.38 H 4.95 N 1.45 Found C 53.24 H 4.75 N 1.29

$[\alpha]_D$+41.3° (c 1.7; CHCl$_3$) $^1$H-NMR(CDCl$_3$) δ 1.76 (s, 3H, AcN)
1.84–2.09(10s, 30H,9 AcO , Ac of Lev)
2.32 (m, 4H, CH$_2$CH$_2$Ac)
3.70 (s, 3H, COOMe)
4.01 (d,1H, J$_{4,5}$=9.8 Hz, H-5e)
4.31 (d,1H, J$_{1,2}$=7.9 Hz, H-1b or H-1d)
4.52 (d,1H, J$_{1,2}$=7.9 Hz, H-1b or 1d)
4.65 (d,1H, J$_{1,2}$=7.9 Hz, H-1c)
4.82 (d,1H, J$_{1,2}$=7.3 Hz, H-1e)
5.03 (dd,1H, J$_{1,2}$=3.8Hz,J$_{2,3}$=1.2 Hz,H-2a)
6.46 (d, 1H, H-1a)
7.15–8.10 (m, 20H, 4 Ph) 8.64 (s,1H, C=NH)
IR (film) 3350 (OH, NH)
1750,1220 (ester)
1680, 1540 (amide)
760, 710 cm$^{-1}$ (Ph)

EXAMPLE 21

Synthesis of O-(methyl 4-O-acetyl-2-O-benzoyl-3-O-levulinoyl-β-Dglucopyranosyluronate) -(1→3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl)-(1→4)-O-(2,3,6-tri-O-acetyl-β-D-glucopyranosyl)-(1→1)-(2S, 3R, 4E)-2-azido-3-O-benzoyl-4-octadecene-1,3-diol (compound 25)

To a solution of compound 24 (1.0 g, 0.52 m mol) and (2S, 3R, 4E)-2-azido-3-O-benzoyl-4-octadecene-1,3-diol 25 (0.47 g, 1.09 m mol) in dichloromethane (10 ml), were added powdered molecular sieves 4 Å (AW-300, 1.5 g) and the mixture was stirred for 5 hrs at room temperature, then cooled to 0° C. Boron trifluoride etherate (0.25 g) was added, and the mixture was stirred for 7 hrs at 0° C. and then filtered. The insoluble material was washed with dichloromethane, and the combined filtrate and washings were washed with M sodium hydrogen carbonate and water, dried (Na$_2$SO$_4$), and concentrated. Column chromatography (40:1 dichloromethane-methanol) of the residue on silica gel (100 g) gave amorphous compound 25 (0.82 g, 72% yield):

Elementary analysis as C$_{109}$H$_{132}$N$_4$O$_{44}$ Calc. C 59.45 H 6.04 N 2.54 Found C 59.30 H 5.75 N 2.35

[α]$_D$+6.0° (c 0.8; CHCl$_3$)

$^1$H-NMR(CDCl$_3$) δ 0.88 (t,3H, J$_{Me,CH2}$=6.6 Hz, MeCH$_2$)
1.23 (s,22H, 22H, 11CH$_2$)
1.70 (s, 3H, AcN)
1.84–2.07(10s, 30H,9 AcO, Ac of Lev)
2.32 (m, 4H, CH$_2$CH$_2$Ac)
3.65 (s, 3H, COOMe)
4.27 (d,1H, J$_{1,2}$=7.9 Hz, H-1a,1b or H-1d)
4.48 (d,1H, J$_{1,2}$=7.5 Hz, H-1a,1b or 1d)
4.51 (d,1H, J$_{1,2}$=7.5 Hz, H-1a,1b or 1d)
4.64 (d,1H, J$_{1,2}$=7.9 Hz, H-1c)
4.82 (d,1H, J$_{1,2}$=7.1 Hz, H-1e)
5.83 (dt,1H, H-5 for sphingosine)
7.15–8.09 (m, 25H, 5 Ph) IR (film) 3380 (NH)
2110 (azide)
2930,2860 (CH)
1750,1230 cm$^{-1}$ (ester)

EXAMPLE 22

Synthesis of O-(methyl 4-O-acetyl-2-O-benzoyl-3-O-levulinoyl-β-D-glucopyranosyluronate)-(1→3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl)-(1→4)-O-(2,3,6-tri-O-acetyl-β-D-glucopyranosyl)-(1→1)-(2S, 3R, 4E)-3-O-benzoyl-2-octadecanamido-4-octadecene-1,3-diol (compound 26-A, n=17) Hydrogen sulfide was bubbled into a stirred solution of compound 25 (700 mg, 0.32 m mol) in aqueous 80% pyridine (50 m ) for 60 hrs at 10° C. The mixture was concentrated, and the residue was stirred with octadecanoic acid (270 mg, 0.95 m mol) and 1-ethyl-3-(3-dimethyl aminopropyl) carbodiimide hydrochloride (WSC, 240 mg, 1.25 m mol) in dry dichloromethane for one night at room temperature. Dichloromethane (50 ml) was added, and the mixture was washed with water, dried (Na$_2$SO$_4$), and concentrated. Column chromatography (40:1 dichloromethane-methanol) of the residue on silica gel (100 g) gave amorphous compound 26-A (n=17) (606 mg, 78% yield):

Elementary analysis as C$_{127}$H$_{168}$N$_2$O$_{45}$ Calc. C 62.45 H 6.93 N 1.15 Found C 62.19 H 6.85 N 1.11

[α]$_D$+14.2° (c 1.0; CHCl$_3$)

$^1$H-NMR(CDCl$_3$) δ 0.88 (t,6H,2MeCH$_2$)
1.25 (s,52H, 26CH$_2$)
1.73 (s, 3H, AcN)
1.84–2.08(10s, 30H,9 AcO , Ac of Lev)
2.32 (m, 4H, CH$_2$CH$_2$Ac)
3.65 (s, 3H, COOMe)
4.41 (d,1H, J$_{1,2}$=7.7 Hz, H-1a,1b or H-1d)
4.50 (d,1H, J$_{1,2}$=7.7 Hz, H-1a, 1b or 1d)
4.64 (d, 1H, J$_{1,2}$=7.9 Hz, H-1c)
4.82 (d, 1H, J$_{1,2}$=7.3 Hz, H-1e)
5.74 (d,1H, NH-Cer)
5.85 (dt, 1H, H-5 for sphingosine)
7.15–8.09 (m, 25H, 5 Ph)
IR (film) 3380 (NH)
2930, 2860 (CH)
1750,1230 (ester)
1680, 1540 cm$^{-1}$ (amide)

Using the same method as above-mentioned, but substituting tetracosanic acid (370 mg, 1.00 m mol) for octadecanoic acid) (270 mg, 0.95 m mol), amorphous O-(methyl 4-O-acetyl-2-O-benzoyl-3-O-levulinoyl-β-D-glucopyranosyl uronate)-(1→3)-O-(2,4,6-tri-O-benzoyl-β-D-galactopyranosyl)-(1→4)-O-(2-acetamido-3,6-di-O-acetyl-2-deoxy-β-D-galactopyranosyl)-(1→3)-O-(2,4,6-tri-O-acetyl-β-D-galactopyranosyl)-(1→4)-(2,3,6-tri-O-acetyl-β-D-glucopyranosyl)-(1→1)-(2S, 3R, 4E)-3-O-benzyl-2-tetracosanamido-4-octadecene-1,3-diol (compound 26-B, n=23) (570 mg, yield 71%) was obtained.

Elementary analysis as C$_{133}$H$_{180}$N$_2$O$_{45}$ Calc. C 63.22 H 7.18 N 1.11 Found C 63.10 H 7.16 N 0.98

[α]$_D$+13.8° (c 1.2; CHCl$_3$)

$^1$H-NMR(CDCl$_3$) δ 0.88 (t,6H,2MeCH$_2$)
1.25 (s,64H, 32CH$_2$)
1.68 (s, 3H, AcN)
1.84–2.08(10s, 30H,9 AcO , Ac of Lev)
2.28 (m, 4H, CH$_2$CH$_2$Ac)
3.65 (s, 3H, COOMe)
4.23 (d,1H, J$_{1,2}$=7.7 Hz, H-1a,1b or H-1d)
4.41 (d,1H, J$_{1,2}$=7.7 Hz, H-1a,1b or H-1d)
4.50 (d,1H, J$_{1,2}$=7.9 Hz, H-1a,1b or 1 d)
4.64 (d,1H, J$_{1,2}$=8.0 Hz, H-1c)
4.82 (d,1H, J$_{1,2}$=7.3 Hz, H-1e)
5.73 (d,1H, NH-Cer)
5.85 (dt, 1H, H-5 for sphingosine)
7.14–8.09 (m, 25H, 5 Ph)
IR (film) 3380 (NH)
2930, 2850 (CH)
1750,1230 (ester)
1680, 1540 cm$^{-1}$ (amide)

EXAMPLE 23

Synthesis of O-(methyl 4-O-acetyl-2-O-benzoyl-β-D-glucopyranosylurorate)-(1→3)-O-(2,4,6-O-benzoyl-β-D-galactopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl)-(1→4)-O-(2,3,6-tri-O-acetyl-β-D-glucopyranosyl)-(-1→1)-(2S, 3R, 4E)-3-O-benzoyl-2-octadecanamido-4-octadecene-1,3-diol (compound 27-A, n=17)

A mixture of compound 26-A (n=17) (300 mg, 0.12 m mol) and hydrazine-aceticacid (55 mg, 0.60 m mol) in ethanol (10 ml) was stirred for 1 h at room temperature. Dichloromethane (50 ml) was added, and the mixture was washed with 1M sodium hydrogen carbonate and water, dried (Na$_2$SO$_4$), and concentrated. Column chromatography (25:1 dichloromethane-methanol) of the residue on silica gel (50 g) gave amorphous compound 27-A (n=17) (282 mg, 98% yield):

Elementary analysis as C$_{122}$H$_{162}$N$_2$O$_{43}$ Calc. C 62.50 H 6.96 N 1.19 Found C 62.20 H 6.91 N 1.16

[α]$_D$+6.1° (c 1.5 ; CHCl$_3$)

$^1$H-NMR(CDCl$_3$) δ 0.88 (t,6H,2MeCH$_2$)
1.25 (s,52H, 26CH$_2$)
1.61 (s, 3H, AcN)
1.85–2.08(9s, 27H,9 AcO )
3.65 (s, 3H, COOMe)
4.24 (d,1H, J$_{1,2}$=8.0 Hz, H-1a,1b or H-1d)
4.41 (d,1H, J$_{1,2}$=7.7 Hz, H-1a,1b or H-1d)
4.53 (d,1H, J$_{1,2}$=7.9 Hz, H-1a,1b or 1d)

4.67 (d,1H, $J_{1,2}$=7.9 Hz, H-1c)
5.74 (d,1H, NH-Cer)
5.86 (dt, 1H, H-5 for sphingosine)
7.18–8.08 (m, 25H, 5 Ph)
   IR (film) 3380 (NH)
2930, 2850 (CH)
1750,1230 (ester)
   1680, 1530 cm$^{-1}$ (amide)
   Using the same procedures as above-mentioned, but substituting compound 26-B (n=23) (300 mg, 0.12 m mol) for compound 26-A (n=17) (300 mg, 0.12 m mol), amorphous O-(methyl 4-O-acetyl-2-O-benzoyl-β-D-glucopyranosyluronate)-(1→3)-O-(2,4,6-tri-O-benzoyl-β-D-glucopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl)-(1→4)-O-(2,3,6-tri-O-acetyl-β-D-glucopyranosyl)-(1→1)-(2S, 3R, 4E)-3-O-benzoyl-2-tetracosanamido-4-octadecene-1,3-diol (compound 27-B, n=23) (285 mg, quantitative yield) was obtained.
   Elementary analysis as $C_{128}H_{174}N_2O_{43}$ Calc. C 63.30 H 7.22 N 1.15 Found C 63.21 H 7.06 N 0.96
   $[α]_D$+6.2° (c 0.8; CHCl$_3$)
   $^1$H-NMR(CDCl$_3$) δ 0.88 (t,6H,2MeCH$_2$)
1.26 (s,64H, 32CH$_2$)
1.60 (s, 3H, AcN)
1.85–2.02(9s, 27H,9 AcO )
3.65 (s, 3H, COOMe)
4.24 (d,1H, $J_{1,2}$=8.1 Hz, H-1a,1b or H-1d)
4.41 (d,1H, $J_{1,2}$=7.7 Hz, H-1a,1b or H-1d)
4.52 (d,1H, $J_{1,2}$=7.9 Hz, H-1a,1b or 1d)
4.67 (d,1H, $J_{1,2}$=7.9 Hz, H1-1c)
5.74 (d,1H, NH-Cer)
5.85 (dt, 1H, H-5 for sphingosine)
7.18–8.08 (m, 25H, 5 Ph)
   IR (film) 3390 (NH ,OH)
2930, 2850 (CH)
1750,1230 (ester)
1680, 1530 cm$^{-1}$ (amide)

EXAMPLE 24 synthesis of O-(methyl 4-O-acetyl-2-O-benzoyl-3-O-sulfo-β-D-glucopyranosyluronate)-(1→3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl)-(1→4)-O-(2,3,6-tri-O-acetyl-β-D-glucopyranosyl)-(1→1)-(2S, 3R, 4E)-3-O-benzoyl-2-octadecanamido-4-octadecene-1,3-diol, sodium salt (compound 28-A, n=17)

A solution of compound 27-A (n=17) (280 mg, 0.12 m mol) and sulfur trioxide-trimethylamine complex (250 mg, 1.8 m mol) in DMF (3 ml) was stirred at 40° C. for 20 hrs and then cooled to room temperature. Directly eluted from a column of LH-20 with 1:1 dichloromethane-methanol, and further a column of Dowex-50×2 (Na$^+$)resin with methanol gave amorphous compound 28-A (n=17) (283 mg, 97% yield):
   Elementary analysis as $C_{122}H_{161}N_2O_{46}S_1Na_1$ Calc. C 59.89 H 6.63 N 1.14 Found C 59.63 H 6.52 N 1.04
   $[α]_D$+11.8° (c 0.6; CHCl$_3$)
   $^1$H-NMR(CDCl$_3$) δ 0.89 (t,6H,2MeCH$_2$)
1.26 (s,52H, 26CH$_2$)
1.60 (s, 3H, AcN)
1.81–2.05(9s, 27H,9 AcO )
3.65 (s, 3H, COOMe)
5.87 (dt, 1H, H-5 for sphingosine)
7.09–8.09 (m, 25H, 5 Ph)
   IR (film) 2930, 2860 (CH)
1750,1230 (ester)
1670, 1540 cm$^{-1}$ (amide)
   Using the same procedures as above-mentioned, but substituting compound 27-B (n=23) (270 mg, 0.11 mol) for compound 27-A (n=17) (280 mg, 0.12 m mol), amorphous O-(methyl 4-O-acetyl-2-O-benzoyl-3-O-sulfo-β-D-glucopyranosyluronate-(1→3)-O-(2,4,6-tri-O-benzoyl-β-D-galactopyranosyl)-(1→4)-O-(2-acetamido)-3,6-di-O-acetyl-2-deoxy-β-D-glucopyranosyl)-(1→3)-O-(2,4,6-tri-O-acetyl-β-D-glucopyranosyl)-(1→4)-O-(2,3,6-tri-O-acetyl-β-D-glucopyranosyl)-(1→1)-(2S, 3R, 4E)-3-O-benzoyl-2-tetracosanamido-4-octadecene-1,3-diol, sodium salt (compound 28-B, n=23) (270 mg, yield 96%) was obtained.
   Elementary analysis as $C_{128}H_{173}N_2O_{46}S_1Na_1$ Calc. C 60.75 H 6.89 N 1.11 Found C 60.70 H 6.78 N 0.85
   $[α]_D$+3.3° (c 0.7; CHCl$_3$)
   $^1$H-NMR(CDCl$_3$) δ 0.88 (t,6H,2MeCH$_2$)
1.26 (s,64H, 32CH$_2$)
1.60 (s, 3H, AcN)
1.83–2.06(9s, 27H,9 AcO )
3.67 (s, 3H, COOMe)
5.85 (dt, 1H, H-5 for sphingosine)
7.15–8.06 (m, 25H, 5 Ph)
   IR (film) 2930, 2850 (CH)
1750,1230 (ester)
1680, 1540 cm$^{-1}$ (amide)

EXAMPLE 25

Synthesis of O-(β-D-glucopyranosyluronic acid))-(1→3)-O-(β-D-galactopyranosyl) -(1→4)-O-(2-acetamido)-2-deoxy-β-D-glucopyranosyl)-(1→3)-O-(β-D-galactopyranosyl)-(1→4)-O-(β-D-glucopyranosyl)-(1→1) -(2S, 3R, 4E)-2-octadecanamido-4-octadecene-1,3-diol, sodium salt (compound 29-A, n=17)

To a solution of compound 27-A (n=17) (140 mg, 59.7 μmol) in THF (5 ml), was added LiOH.H$_2$O (13 mg, 0.13 m mol) in H$_2$O (1 ml), and the mixture was stirred for 3 hrs at 5° C., and concentrated at 30° C. THF (7 ml), methanol (7 ml) and sodium methox1d)e (10 mg) were added, the mixture was stirred for one night at 10° C., and purified on a column of sephadex LH-20 in 6:4:1=CHCl$_3$:MeOH:H$_2$O to give compound 29-A (n=17) (52 mg, 61% yield):
   $^1$H-NMR(49:1 Me$_2$SO-J$_6$-D$_2$O, 60° C.)
   δ 0.91 (t,6H,2MeCH$_2$)
1.29 (s,52H, 26CH$_2$)
1.80 (s, 3H, AcN)
5.80 (m, 3H, H-5 for sphingosine)
   Using the same procedures as above-mentioned, but substituting compound 27-B (n=23) (150 mg, 61.8 μmol) for compound 27-A (n=17) (140 mg, 59.7 μmol), amorphous O-(β-D-glucopyranosyluronic acid))-(1→3)-O-(β-D-galactopyranosyl)-(1→4)-O-(2-acetamido)-2-deoxy-β-D-glucopyranosyl)-(1→3)-O-(β-D-galactopyranosyl)-(1→4)-O-(β-D-glucopyranosyl)-(1→1)-(2S, 3R, 4E)-2-tetracosanamido-4-octadecene-1,3-diol sodium salt (compound 29-B, n=23) (48.7 mg, 52% yield) was obtained.
   $^1$H-NMR ((49:1 Me$_2$SO-J$_6$-D$_2$O, 60° C.)
   δ 0.90 (t,6H,2MeCH$_2$)
1.26 (s,64H, 32CH$_2$)
1.77 (s, 3H, AcN)

5.82 (m, 1H, H-5 for sphingosine)

EXAMPLE 26

Synthesis of O-(3-O-sulfo-β-D-glucopyranosyluronic acid)-(1→3) -O-(β-D-galactopyranosyl)-(1→4)-O-(2-acetamido)-2-deoxy-β-D-glucopyranosyl)-(1→3)-O-(β-D-galactopyranosyl-(1→4)-O-(β-D-glucopyranosyl)-(1→1)-(2S, 3R, 4E)-2-octadecanamido-4-octadecene-1,3-diol, disodium salt (compound 30-A, n=17) Compound 28-A (n=17) (140 mg, 57.2 μmol) was subjected to deacylation and saponification as in Example 25 to obtain 67.6 mg of compound 30-A (n=17)(77% yield):

$^1$H-NMR(49:1 Me$_2$SO-J$_6$-D$_2$O, 60° C.)
δ 0.89 (t,6H,2MeCH$_2$)
1.28 (s,52H, 26CH$_2$)
1.80 (s, 3H, AcN)
5.78 (m, 1H, H-5 for sphingosine)

Using the same procedures as above-mentioned, but substituting compound 28-B (n=23) (130 mg, 51.4 μmol) for compound 28-A (n=17) (140 mg, 57.2 μmol), O-(3-O-sulfo-β-D-glucopyranosyluronic acid)-1→3)-O-(β-D-galactopyranosyl)-(1→4)-O-(2-acetamido)-2-deoxy-β-D-glucopyranosyl)-(1→3)-O-(β-D-galactopyranosyl)-(1→4)-O-(β-D-glucopyranosyl)-(1→1)-(2S, 3R, 4E)-2-tetracosanamido-4-octadecene-1,3-diol, disodium salt (compound 30-B, n=23) (56.3 mg, 65% yield) was obtained.

$^1$H-NMR ((49:1 Me$_2$SO-J$_6$-D$_2$O, 60° C.)
δ 0.88 (t,6H,2MeCH$_2$)
1.27 (s,64H, 32CH$_2$)
1.77 (s, 3H, AcN)
5.81 (m, 1H, 1H, H-5 for sphingosine)

EXAMPLE 27

Synthesis of 2-(trimethyl silyl)ethyl O-(4-O-acetyl-3,6-di-O-benzyl-2-deoxy-2-phthalimido-β-D-glucopyranosyl)-1→3)-2,4,6-tri-O-benzyl-βD-galactopyranoside (compound 31) To a solution of compound 17 (4.5 g, 6.7 m mol) in dichloromethane (20 ml), were added 2-(trimethyl siliyl) ethyl 2,4,6-tri-O-benzyl-β-D-galactopyranoside (compound 9) (7.8 g, 14.2 m mol), and powdered molecular sieves 4 521 (4.0 g), and the mixture was stirred for 5 hrs at room temperature (mixture A)

A solution of trimethylsilyl trifluoromethane sulfonate (TMSOTf) (0.4 g, 1.8 m mol) in dichloromethane (2 ml) was treated with powdered molecular sieves 4 Å (0.7 g) as above, and then added to mixture A at −20° C. After stirred for 0.5 h at −20° C., the mixture was neutralized with triethylamine and filtered. The residue was washed with dichloromethane and the combined filtrate and washings were concentrated. Column chromatography (1:3.5 ethyl acetate-hexane) of the residue on silica gel (300 g) afforded compound 31 (6.7 g, 94% based on compound 17) as crystals. Recrystallization from ethanol gave needles:

Elementary analysis as C$_{62}$H$_{69}$N$_1$O$_{13}$Si$_1$ Calc. C 69.97 H 6.53 N 1.32 Found C 69.93 H 6.52 N 1.11

M.P. 89.0°~91.0° C.

[α]$_D$+9.3° (c 0.6; CHCl$_3$) $^1$H-NMR(CDCl$_3$) δ 0.81 (m, 2H, Me$_3$SiCH$_2$CH$_2$)
1.94 (s, 3H, AcO)
3.94 (d, 1H, J$_{3,4}$=3.0 Hz, H-4 for Gal)
4.33 (d, 1H, J$_{1,2}$=7.9 Hz, Hz, H-1 for Gal)
5.16 (dd, 1H, J$_{3,4}$=9.0 Hz, J$_{4,5}$=9.9 Hz, H-4 for GlcN)
5.48 (d, 1H, J$_{1,2}$=8.2 Hz H-1 for Glc N)

7.17–7.51(m, 29H, 5 Ph, Phathaloyl-H)
IR (KBr) 1750,1230 (ester)
1720(imide)
860 and 840 (TMS)
740, 720, 700 cm$^{-1}$ (Ph)

EXAMPLE 28

Synthesis of 2-(trimethyl silyl)ethyl-(2-acetamido)-3,6-di-O-benzyl-2-deoxy-β-D-glucopyranosyl)-(1→3)-2,4,6-tri-O-benzyl-β-D-galactopyranoside (compound 32)

A solution of compund 31 (6.5 g, 6.1 m mol) in methanol (70 ml) was stirred with sodium methoxide (100 mg) for 2 hrs at room temperature. The mixture was treated with Amberlite IR-120 (H$^+$) rezin and concentrated, and a solution of the residue in aqueous 95% ethanol (70 ml) was heated for 5 hrs under reflux. The precipitate was collected and washings were concentrated. The concentrated residue was treated with acetic anhydride (5 ml) in methanol (70 ml) for 1 h at room temperature. Pyridine (10 ml) was added, the mixture was concentrated, and a solution of the thus obtained residue in dichloromethane (250 ml) was successively washed with 2M hydrochloric acid), water, and 1M sodium carbonate, dried (Na$_2$SO$_4$) and concentrated. Column chromatography (1:1 ethyl acetate-hexane) of the residue on silica gel (300 g) afforded compound 32 (4.8 g, 85% yield) as crystals. Recrystallization from ethanol gave needles:

Elementary analysis as C$_{54}$H$_{67}$N$_1$O$_{11}$Si$_1$ Calc. C 69.43 H 7.23 N 1.50 Found C 69.17 H 7.22 N 1.39

M.P. 112.5°~114.0° C.

[α]$_D$−15.8° (c 0.4 ; CHCl$_3$)
$^1$H-NMR(CDCl$_3$) δ 0.99 (m, 2H,Me$_3$SiCH$_2$CH$_2$)
1.52 (s, 3H, AcN)
7.20–7.36(m, 25H, 5 Ph)
IR (KBr) 3450–3300 (NH, OH)
1660,1530 (amide)
860 and 840 (TMS)
740, 700 cm$^{-1}$ (Ph)

EXAMPLE 29

Synthesis of 2-(trimethyl silyl)ethyl O-(methyl 4-O-acetyl-2-O-benzoyl-3-O-levulinoyl-β-D-glucopyranosyluronate)-(1→3)-O-(2,4,6-tri-O-benzoyl-β-D-galactopyranosyl)(1→4)-O-(2-acetamido)o-3,6-di-O-benzyl-2-deoxy-β-D-glucopyranosyl)-(1→3)-2,4,6-tri-O-benzyl-β-D-galactopyranoside (compound 33)

To a solution of compound 13 (2.8 g, 2.61 m mol) in dichloromethane (15 ml), were added compound 32 (4.2 g, 4.50 m mol), and powdered molecular sieves 4 Å (2.3 g), and the mixture was stirred for 5 hrs at room temperature (mixture A). A solution of TMSOTf (87 mg, 0.3 m mol) in dichloromethane (1.5 ml) was treated with powdered molecular sieves 4 Å (0.5 g) as above, and then added to mixture A at −10° C. After stirred for one night at room temperature, the mixture was neutralized with triethylamine and filtered. The residue was washed with dichloromethane and the combined filtrate and washings were concentrated. Column chromatography (1:1 ethyl acetate-hexane) of the residue on silica gel (200 g) afforded compound 33 (4.4 g, 92% based on compound 13) as a syrup, together with recovered compound 32 (2.0 g, 48%):

Elementary analysis as C$_{102}$H$_{111}$N$_1$O$_{29}$Si$_1$ Calc. C 66.47 H 6.07 N 0.76 Found C 66.37 H 5.81 N 0.67

[α]$_D$+3.4° (c 0.8; CHCl$_3$)
$^1$H-NMR(CDCl$_3$) δ 0.97 (m, 2H,Me$_3$SiCH$_2$CH$_2$)
1.97 (s, 3H, AcO)
3.70 (s, 3H, COOMe)
5.53 (dd,1H, H-2f)
5.77 (d, 1H, H-4f)
7.00–8.06 (m, 45H, 9 Ph)
IR (film) 3390 (NH)
1730,1270 (ester)
1680, 1530 (amide)
860, 840 (TMS)
750, 710 cm$^{-1}$ (Ph)

EXAMPLE 30

Synthesis of 2-(trimethyl silyl)ethyl O-(methyl 4-O-acetyl-2-O-benzoyl-3-O-levulinoyl-β-D-glucopyranosyluronate)-(1→3)-O-(2,4,6-tri-O-benzoyl-β-D-galactopyranosyl)-(1→4)-O-(2-acetamido-3,6-di-O-benzyl-2-deoxy-β-D-glucopyranosyl)-(1→3)-2,4,6-tri-O-benzoyl-β-D-galactopyranoside (compound 34)

A solution of compound 33 (4.5 g, 2.44 m mol) in methanol (50 ml) and ethyl acetate (10 ml) was hydrogenolyzed in the presence of 10% Pd-C (2.0 g) for 24 hrs at room temperature, then filtered and concentrated. The residue was dissolved in pyridine (50 ml) and added with 4-dimethylaminopyridine (2.0 g), and then added with benzoic anhydride (3.3 g) at 70° C. The mixture was stirred for 1.5 hrs at 70° C. and concentrated, and a solution of the residue in dichloromethane (300 ml) was successively washed with 2M hydrochloric acid), water, and 1M sodium carbonate, dried (Na$_2$SO$_4$) and concentrated. Column chromatography (50:1 dichloromethane-methanol) of the residue on silica gel (200 g) afforded compound 34 (3.7 g, 79% yield) as an amorphous mass:

Elementary analysis as C$_{102}$H$_{101}$N$_1$O$_{34}$Si$_1$ Calc. C 64.04 H 5.32 N 0.73 Found C 63.79 11 5.13 N 0.58
[α]$_D$+32.2° (c 0.9, CHCl$_3$)
$^1$H-NMR (CDCl$_3$) δ 0.84 (m, 2H, Me$_3$SiCH$_2$CH$_2$)
1.99 (s, 3H, AcO)
3.71 (s, 3H, COOMe)
4.48 (d, 1H, J$_{1,2}$=8.1 Hz, H-1d or 1f)
4.59 (d, 1H, J$_{1,2}$=8.1 Hz, H-1d or 1f)
4.71 (d, 1H, J$_{1,2}$=7.3 Hz, H-1g)
4.87 (d, 1H, J$_{1,2}$=8.2 Hz, H-1e)
4.98 (dd, 1H, J.H-2g) 5.73 (d
6.90–8.04 (m, 45H, 9 Ph)
IR (film) 3370 (NH)
1740, 1270 (ester)
1680, 1540 (amide)
710, 690 cm$^{-1}$ (Ph)

EXAMPLE 31

Synthesis of O-(methyl 4-O-acetyl-2-O-benzoyl-3-O-levulinoyl-β-D -glucopyranosyltironate)-(1→3)-O-(2,4,6-tri-O-benzoyl-β-D-galactopyranosyl) -(1→4)-O-(2-acetamido-3,6-di-O-benzoyl-2-deoxy-β-D-glucopyranosyl) -(1→3)-2,4,6-tri-O-benzoyl-β-D-galactopoyranose (compound 35)

To a solution of compound 34 (3.8 g, 1.99 m mol) in dichloromethane (30 ml), was added trifluoroacetic acid) (9 ml) at 0° C., and the mixture was stirred for 3 hrs at room temperature, and concentrated. Column chromatography (30:1 dichloromethane-methanol) of the residue on silica gel (200 g) gave compound 35 (3.4 g, 94% yield) as a syrup:

Elementary analysis as C$_{97}$H$_{89}$N$_1$O$_{34}$ Calc. C 64.27 H 4.95 N 0.77 Found C 64.17 H 4.70 N 0.50
[α]$_D$+44.3° (c 0.8, CHCl$_3$)
IR (film) 3380 (NH, OH)
1730, 1270 (ester)
710, 690 cm$^{-1}$ (Ph)

EXAMPLE 32

Synthesis of O-(methyl 4-O-acetyl-2-O-benzoyl-3-O-levulinoyl-β-D-glucopyranosyluronate)-(1→3)-O-(2,4,6-tri-O-benzoyl-β-D-galactopyranosyl) -(1→4)-O-(2-acetamido-3,6-di-O-benzoyl-2-deoxy-β-D-glucopyranosyl) -1→3)-2,4,6-tri-O-benzoyl-β-Dgalactopyranosyl trichloroacetimidate (compound 36)

To a solution of compound 35 (3.5 g, 1.93 m mol) in dichloromethane (40 ml) and trichloroacetonitrile (5 ml), was added 1,8-diazabicyclo[5.4.0]undec-7-ene (DBU, 60 mg) at −10° C., and the mixture was stirred for 3 hrs at 0° C. and directly eluted from a column of silica gel (200 g) with ethyl acetate-hexane (2:1) to give amorphous compound 36 (3.5 g, 92% yield):

Elementary analysis as C$_{99}$H$_{89}$N$_2$O$_{34}$Cl$_3$ Calc. C 60.76 H 4.58 N 1.43 Found C 60.74 H 4.32 N 1.14
[α]$_D$+48.3° (c 0.9, CHCl$_3$)
$^1$H-NMR (CDCl$_3$) δ 1.70 (s, 3H, AcN)
1.99 (s, 3H, AcO)
2.28 (m, 4H, CH$_2$CH$_2$Ac)
3.70 (s, 3H, COOMe)
4.51 (d, 1H, J$_{1,2}$=7.7 Hz, H-1e or 1f or 1g)
4.72 (d, 1H, J$_{1,2}$=7.2 Hz, H-1e or 1f or 1g)
4.89 (d, 1H, J$_{1,2}$=8.2 Hz, H-1e or 1f or 1g)
5.58 (d, 1H, J$_{3,4}$=2.8 Hz, H-4d or f)
5.79 (dd, 1H,J$_{2,3}$=10.1 Hz, H-2d)
5.92 (d, 1H, J$_{3,4}$=3.7 Hz, H-4d or f)
6.69 (d, 1H, J$_{1,2}$=3.8 Hz, H-1d)
6.90–8.01 (m, 45H, 9 Ph)
8.51 (s, 1H, C═NH)
IR (film) 3390 (NH)
1730, 1270 (ester)
1680, 1590 (amide)
710, 690 cm$^{-1}$ (Ph)

EXAMPLE 33

Synthesis of 2-(trimethyl silyl)ethyl O-(methyl 4-O-acetyl-2-O-benzoyl-3-O-levulinoyl-β-D-glucopyranosyluronate)-(1→3)-O-(2,4,6-tri-O-benzoyl-β-D-galactopyranosyl)-(1→4)-O-(2-acetamido-3,6-di-O-benzoyl -2-deoxy-β-D-glucopyranosyl)-(1→3)-O-(2,4,6-tri-O-benzoyl-β-D-galactopyranosyl) -(1→4)-O-(2-acetamido)-3,6-di-O-benzyl-2-deoxy-β-D-glucopyranosyl) -(1→3)-O-(2,4,6-tri-O-benzyl-β-D-galactopyranosyl)-(1→4)-2,3,6-tri-O-benzyl-β-D-glucopyranoside (compound 37)

To a solution of compound 36 (2.6 g, 1.33 m mol) in dichloromethane (15 ml), were added compound 20 (4.0 g, 2.93 m mol), and powdered molecular sieves 4 Å (2.0 g), and the mixture was stirred for 5 hrs at room temperature (mixture A). A solution of TMSOTf (60 mg, 0.27 m mol) in dichloromethane (1 ml) was treated with powdered molecular sieves 4 Å (0.6 g) as above, and then added to mixture A at room temperature. After stirred for one night at room temperature, the mixture was neutralized with triethylamine and filtered. The residue was washed with dichloromethane and the combined filtrate and washings were concentrated. Column chromatography (2:1 ethyl acetate-hexane) of the residue on silica gel (250 g) afforded compound 37 (4.0 g, 95%) as an amorphous mass, together with recovered compound 20 (1.8 g, 45% yield):

Elementary analysis as $C_{178}H_{182}N_2O_{49}Si_1$ Calc. C 67.63 H 5.80 N 0.89 Found C 67.43 H 5.56 N 0.75

$[\alpha]_D$+13.3° (c 0.9, $CHCl_3$) $^1$H-NMR ($CDCl_3$) δ 1.00 (m, 2H, $Me_3SiCH_2CH_2$)
1.73 (s, 3H, AcN)
1.76 (s, 3H, AcN)
1.94 (s, 3H, AcO or Ac of Lev)
2.00 (s, 3H, AcO or Ac of Lev)
2.26 (m, 4H, $CH_2CH_2Ac$)
3.63 (s, 3H, COOMe)
6.91–7.99 (m, 85H, 17 Ph)
IR (film) 3390 (NH)
1740, 1270 (ester)
1680, 1540 (amide)
740, 710 $cm^{-1}$ (Ph)

EXAMPLE 34

Synthesis of 2-(tirmethyl silyl)ethyl O-(methyl 4-O-acetyl-2-O-benzoyl-3-O-levulinoyl-β-D-glucopyranosyluronate)-(1→3)-O-(2,4,6-tri-O-benzoyl-β-D-galactopyranosyl)-(1→4)-O-(2-acetamido)-3,6-di-O-benzyl -2-deoxy-β-D-glucopyranosyl)-(1→3)-O-(2,4,6-tri-O-benzoyl-β-D-galactopyranosyl) -(1→4)-O-(2-acetamido)-3,6-di-O-acetyl-2-deoxy-β-D-glucopyranosyl) -1→3)-O-(2,4,6-tri-O-acetyl-β-D-galactopyranosyl)-(1→4)-2,3,6-tri-O-acetyl-ββ-D-glucopyranoside (compound 38)

A solution of compound 37 (3.9 g, 1.23 m mol) in methanol (40 ml) and ethyl acetate (20 ml) was hydrogenolyzed in the presence of 10% Pd-C (2.0 g) for 24 hrs at room temperature, then filtered and concentrated. The residue was acetylated with acetic anhydride (20 ml)-pyridine (40 ml) for 20 hrs at room temperature, and concentrated. The product was purified by chromatography on a column of silica gel (200 g) with an ethyl acetate elunt, to obtain compound 38 (3.4 g, quantitative yield) as an amorphous mass:

Elementary analysis as $C_{138}H_{150}N_2O_{57}Si_1$ Calc. C 59.69 H 5.45 N 1.01 Found C 59.66 H 5.34 N 0.98

$[\alpha]_D$+17.6° (c 0.9, $CHCl_3$)
$^1$H-NMR ($CDCl_3$) δ 0.93 (m, 2H, $Me_3SiCH_2CH_2$)
1.85 (s, 3H, AcN)
1.86 (s, 3H, AcN)
1.97–2.08 (10s, 30H,9 AcO or Ac of Lev)
2.30 (m, 4H, $CH_2CH_2Ac$)
3.70 (s, 3H, COOMe)
4.56, 4.61, 4.71 (3d, 3H, $J_{1,2}$=7.5~7.9 Hz, H-1a or 1b or 1~g)
5.55 (d,1H, $J_{3,4}$=3.3 Hz, H-4 b or d or f)
5.72 (d, 1H, H-4 b or d or f)
6.90–8.00 (m, 45H, 9 Ph)
IR (film) 3380 (NH)
1740, 1270 (ester)
1680, 1540 (amide)

EXAMPLE 35

Synthesis of O-(methyl 4-O-acetyl-2-O-benzoyl-3-O-levulinoyl-β-D-glucopyranosyluronate) -(1→3)-O-(2,4,6-tri-O-benzoyl-β-D-galactopyranosyl)-(1→4)-O-(2-acetamido-3,6-di-O-benzyl-2-deoxy-β-D-glucopyranosyl)-(1→3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3) -O-2,3,6-tri-O-acetyl-β-D-glucopyranosyl)-(1→4)-2,3,6-tri-O-acetyl -β-D-glucopyranoside (compound 39)

To a solution of compound 38 (3.2 g, 1.15 m mol) in dichloromethane (30 ml), was added trifluoroacetic acid) (7 ml) at 0° C., and the mixture was stirred for 3 hrs at room temperature, and concentrated. Column chromatography (eluted with ethyl acetate) of the residue on silica gel (150 g) gave compound 39 (2.6 g, 85% yield) as a syrup:

Elementary analysis as $C_{133}H_{138}N_2O_{57}$ Calc. C 59.68 H 5.20 N 1.05 Found C 59.52 H 4.99 N 0.94

$[\alpha]_D$+29.1° (c 1.9 , $CHCl_3$)
IR (film) 3380 (OH)
1730, 1270 (ester)
1680, 1540 (amide)
760, 710, 690 $cm^{-1}$ (Ph)

EXAMPLE 36

Synthesis of O-(methyl 4-O-acetyl-2-O-benzoyl-3-O-levulinoyl-β-D-glucopyranosyluronate) -(1→3)-O-(2,4,6-tri-O-benzoyl-β-D-galactopyranosyl)-(1→4)-O-(2-acetamido-3,6-di-O-benzyl -2-deoxy-β-D-glucopyranosyl)-(1→3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3) -(2,4,6-tri-O-acetyl-β-D-galactopyranosyl)-(1→4)-2,3,6-tri-O-acetyl-β-D-glucopyranosyl trichloroacetimidate (compound 40)

To a solution of compound 39 (3.0 g, 1.12 m mol) in dichloromethane (60 ml) and trichloroacetonitrile (5.0 ml), was added 1,8-diazabicyclo [5.4.0]undec-7-ene (DBU, 34 mg) at 0° C., and the mixture was stirred for 5 hrs at 0° C. and directly eluted from a column of silica gel (100 g) with ethylacetate-hexane (6:1) to give amorphous compound 40 (2.8 g 90% yield):

Elementary analysis as $C_{135}H_{138}N_3O_{57}Cl_3$ Calc. C 57.48 H 4.93 N 1.49 Found C 57.23 H 4.86 N 1.37

$[\alpha]_D$+32.7° (c 0.4, $CHCl_3$)
$^1$H-NMR ($CDCl_3$) δ 1.69 (s, 3H, AcN)
1.73 (s, 3H, AcN)
1.86–2.09 (10s, 30H,9 AcO or Ac of Lev)
2.34 (m, 4H, $CH_2CH_2Ac$)
3.70 (s, 3H, COOMe)
4.48, 4.55, 4.62, 4.71, 4.82 (5d, 5H, $J_{1,2}$=7.1~18.1 Hz, H-1b~g)
5.73 (d,1H, $J_{3,4}$=3.3 Hz, H-4 b or d or f)
6.46 (d, 1H, $J_{1,2}$=3.8 Hz,H-1a )
6.93–8.00 (m, 45H, 9 Ph)
8.64 (s, 1H, C=NH)
IR (film) 3480 (NH)
1730, 1270 (ester)
1680, 1540 $cm^{-1}$ (amide)

EXAMPLE 37

Synthesis of O-(methyl-4-O-acetyl-2-O-benzoyl-3-O-levulinoyl-β-D -glucopyranosyluronate)-(1→3)-O-(2,4,6-tri-O-benzoyl-β-D-galactopyranosyl)-(1→4) -O-(2-acetamido)-3,6-di-O-benzyl-2-deoxy-β-D-glucopyranosyl)-(1→3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl) -(1→4)-O-(2,3,6-tri-O-acetyl-β-D-glucopyranosyl)-(1→1)-(2S, 3R, 4E)-2-azido-3-O-benzoyl-4-octadecene-1, 3-diol (compound 41)

To a solution of compound 40 (1.0 g , 0.35 m mol) and (2S, 3R, 4E)-2-azido-3-O -benzoyl-4-octadecene-1,3-diol (0.30 g, 0.70 m mol) in dichloromethane (7 ml), were added powdered molecular sieves 4 Å (AW-300, 1.2 g) and the mixture was stirred for 5 hrs at room temperature, then cooled to 0° C. Boron trifluoride etherate (0.17 g) maintained at 0° C. was added, and the mixture was stirred for 7 hrs at 0° C. and then filtered. The insoluble material was washed with dichloromethane, and the combined filtrate and washings were washed with 1M Sodium hydrogen carbonate and water, dried ($Na_2SO_4$), and concentrated. Column chromatography (30:1 dichloromethane-methanol) of the residure on silica gel (100 g) gave amorphous compound 41 (0.67 g, 61% yield)

Elementary analysis as $C_{158}H_{175}N_5O_{59}$ Calc. C 61.45 H 5.71 N 2.27 Found C 61.40 H 5.60 N 2.16

$[\alpha]_D$+9.0° (c 0.6, $CHCl_3$)

$^1$H-NMR ($CDCl_3$) δ 0.87 (t, 3H, $J_{ME,CH2}$=6.6 Hz, $MeCH_2$)

1.23 (s, 22H, 11$CH_2$)

1.85 (s, 3H, AcN)

1.86 (s, 3H, AcN)

1.94–2.08 (10 s, 30H,9 AcO or Ac of Lev)

2.30 (m, 4H, $CH_2CH_2Ac$)

3.62 (s, 3H, COOMe)

4.55,4.61,4.71,4.81 (4d, 4H, $J_{1,2}$=7.1 ~8.1 Hz, H-1a~g)

5.74 (d,1H, H-4 b or d or f)

5.91 (dt, 1H, H-5 for sphingosine)

6.90–8.05 (m, 45H, 9 Ph)

IR (film) 3380 (NH)

2110 (azide)

2930, 2860 (CH)

1730, 1270 cm$^{-1}$ (ester)

EXAMPLE 38

Synthesis of O-(methyl 4-O-acetyl-2-O-benzoyl-3-O-levulinoyl-β-D -glucopyranosyluronate)-(1→3)-O-(2,4,6-tri-O-benzoyl-β-D-galactopyranosyl)-(1→4)-O-(2-acetamido-3,6-di-O-benzoyl-2-deoxy-β-Dglucopyranosyl) -(1 →3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl)-(1→4)-O-(2,3,6-tri-O-acetyl-β-D-glucopyranosyl)-(1→1) -(2S, 3R, 4E)-3-O-benzoyl-2-octadecanamido-4-octadecene-1,3diol (compound 42-A, n=17) Hydrogen sulfide was bubbled into a stirred solution of compound 41 (700 mg, 0.21 m mol) in aqueous 80% pyridine (50 ml) for 70 hrs at 10° C.

The mixture was concentrated, and the residue was stirred with octadecanoic acid (210 mg, 0.74 m mol) and 1-ethyl-3-(3-dimethylaminopropyl) carbodiimide hydrochloride (WSC, 192 mg, 1.00 m mol) in dry dichloromethane for one night at room temperature. Dichloromethane (50 ml) was added, and the mixture was washed with water, dried ($Na_2SO_4$), and concentrated. Column chromatography (45:1 dichloromethane-methanol) of the residue on silica gel (100 g) gave amorphous compound 42-A (n=17) (490 mg, 65% yield):

Elementary analysis as $C_{176}H_{211}N_3O_{60}$ Calc. C 63.51 H 6.39 N 1.26 Found C 63.38 H 6.30 N 1.09

$[\alpha]_D$=22.5° (c 0.7, $CHCl_3$)

$^1$H-NMR ($CDCl_3$) δ 0.88 (t, 6H,2$MeCH_2$)

1.25 (s, 52H, 26$CH_2$)

1.84 (s, 6H, 2 AcN)

1.92–2.09 (9s, 27H,9 AcO )

2.29 (m, 4H, $CH_2CH_2Ac$)

3.70 (s, 3H, COOMe)

4.41, 4.47, 4.54, 4.61, 4.71 (5d, 5H, $J_{1,2}$=7.3~7.9 Hz, H-1a~g)

5.84 (dt,1H, H-5 for sphingosine)

6.90–8.00 (m, 50H, 10 Ph)

IR (film) 3380 (NH) 2930, 2860 (CH) 1740, 1270 (ester) 1680, 1540 (amide) 760,710,690 cm$^{-1}$ (Ph)

EXAMPLE 39

Synthesis of O-(methyl 4-O-acetyl-2-O-benzoyl-β-D-glucopyranosyluronate) -(1→3)-O-(2,4,6-tri-O-benzoyl-β-D-galactopyranosyl)-(1→4)-O-(2-acetamido -3,6-di-O-benzoyl-2-deoxy-β-D-glucopyranosyl)-(1→3)-O-(2,4,6-tri-O-benzyl -β-D-galactopyranosyl)-(1→4)-O-(2-acetamido-3,6-di-O-acetyl-2-deoxy-β-D-glucopyranosyl)-(1→3)-O-(2, 4,6-tri-O-acetyl-β-D-galactopyranosyl)-(1→4)-O-(2, 3,6-tri-O-acetyl-β-D-glucopyranosyl)-(1→1)-(2S, 3R, 4E)-3-O-benzoyl-2-octadecanamido-4-octadecene-1,3-diol (compound 43-A, n=17)

A mixture of compound 42-A (n=17) (270 mg, 81.1 μmol) and hydrazine-acetic acid (40 mg, 0.43 m mol) in ethanol (8 ml) was stirred for 1 h at room temperature. Dichloromethane (50 ml) was added, and the mixture was washed with 1M sodium hydrogen carbonate and water, dried ($Na_2SO_4$), and concentrated. Column chromatography (30:1 dichloromethane-methanol) of the residue on silica gel (45 g) gave amorphous compound 43-A (n=17) (260 mg, quantitative yield):

Elementary analysis as $C_{171}H_{205}N_3O_{58}$ Calc. C 63.58 H 6.40 N 1.30 Found C 63.53 M 6.21 N 1.12

$[\alpha]_D$=14.7° (c 0.7, $CHCl_3$ $^1$-NMR ($CDCl_3$) δ 0.88 (t, 6H,2$MeCH_2$)

1.25 (s, 52H, 26$CH_2$)

1.84 (s, 6H,2 AcN)

1.98–2.08 (9s, 27H,9 AcO )

3.62 (s, 3H, COOMe)

5.85 (dt,1H, H-5 for sphingosine)

6.93–8.02 (m, 50H, 10 Ph)

IR (film) 3380 (NH, OH))

2930, 2860 (CH)

1740, 1270 (ester)

1680, 1540 (amide)

760,720,700 cm$^{-1}$ (Ph)

EXAMPLE 40

Synthesis of O-(β-D-glucopyranosyluronic acid)-(1→3)-O-(β-D-galactopyranosyl)-(1→4)-O-(2-acetamido-2-deoxy-β-D-glucopyranosyl)-(1→3)-O-(-β-D-galactopyranosyl)-(1→4)-O-(2-acetamido-2-deoxy-β-D-glucopyranosyl)-(1→3)-O-(β-D-galactopyranosyl)-(1→4)-O-(β-D-glucopyranosyl)-(1→1)-(2S, 3R, 4E)-2-octadecanamido-4-octadecene-1,3-diol, sodium salt (compound 45-A, n=17)

To a solution of compound 43-A (n=17) (120 mg, 37.1 μmol) in THF (5 ml), was added $LiOH.H_2O$ (10 mg, 0.24 m mol) in $H_2O$ (1 ml), and the mixture was stirred for 3 hrs at 5° C., and concentrated at 30° C. THF (7 ml), Methanol (7 ml) and sodium methoxide (10 mg) were added, and the mixture was stirred for one night at 10° C., and purified on a column of Sephadex LH-20 in 7:3:1 ($CHCl_3$, methanol, $H_2O$) to give compound 45-A (n=17) (55 mg, 82% yield):

$^1$-NMR ($CDCl_3$) (49:1 $Me_2SO-d_6-D_2O$, 60° C.)

δ 0.85(t, 6H,2$MeCH_2$)

1.24 (s, 52H, 26$CH_2$)

1.84–1.85 (s, 6H,2 AcN)

EXAMPLE 41

Synthesis of O-(methyl 4-O-acetyl-2-O-benzoyl-3-O-sulfo-β-D-glucopyranosyluronate) -(1→3)-O-(2,4,6-tri-O-benzoyl-β-D-galactopyranosyl) -(1→4)-O-(2-acetamido-3,6-di-O-benzoyl-2-deoxy-β-D-glucopyranosyl) -1→3)-O-(2,4,6-tri-O-benzoyl-β-D-galactopyranosyl)-(1→4O-(2-acetamido-3,6-di-O-acetyl-β-D-glucopyranosyl)-1→3)-O-(2,4,66-tri-O-acetyl-2-deoxy-β-D-galactopyranosyl)-(1→4)-O-(2,3,6-tri-O-acetyl-β-D-glucopyranosyl)-(1→1)-(2S, 3R, 4E)-3-O-benzoyl-2-octadecanamido-4-octadecene-1,3-diol, sodium salt (compound 44-A, n=17)

A solution of compound 43-A(n=17) (230 mg, 71.2 μmol) and sulfur trioxide-trimethylamine complex (158 mg, 1.14 m mol) in DMF (3 ml) was stirred at 45° C. for 24 hrs and then cooled to room temperature. Directly eluted from a column of LH-20 with 1:1 dichloromethane methanol, and then a column of Dowex-50×2 (Na$^+$) resin with methanol gave amorphous compound 44-A (n=17) (218 mg , 92% yield)

Elementary analysis as $C_{171}H_{204}N_3O_{61}Na_1$ Calc. C 61.63 H 6.17 N 1.26 Found C 61.39 H 6.12 N 1.25

$[\alpha]_D$+12.1° (c. 0.41 , CHCl$_3$)

$^1$H-NMR (CDCl$_3$) δ 0.88 (t, 6H,2MeCH$_2$)
1.25 (s, 52H, 26CH$_2$)
1.85–1.86 (2s, 6H,2 AcN)
1.92–2.08 (9s, 27H, 9 AcO)
3.62 (s, 3H, COOMe)
6.92–8.01 (m, 50H, 10 Ph)
IR (film) 3390 (NH)
2930, 2850 (CH)
1750, 1270 (ester)
1680, 1540 (amide)
750,710,700 cm$^{-1}$ (Ph)

EXAMPLE 42

Synthesis of O-(3-O-sulfo-β-D-glucopyranosyluronic acid)-(1→3)-O-(β-D-galactopyranosyl)-(1→4)-O-(2-acetamido-2-deoxy-β-D-glucopyranosyl)-(1→3)-O-(β-D-galactopyranosyl)-(1→4)-3-O-(2-acetamido-2-deoxy-β-D-glucopyranosyl)-(1→3)-O-(β-D-galactopyranosyl)-(1→4)-O-(β-D-glucopyranosyl)-(1→1)-(2S, 3R, 4E)-2-octadecanamido-4-octadecene-1,3-diol, disodium salt (compound 46-A, n=17) Deacylation and saponification of compound 44-A (n=17) (110 mg, 33.0 μmol), as described for Example 40 gave compound 46-A (n=17) (49 mg, 78% yield):

$^1$H-NMR (CDCl$_3$) (49:1 Me$_2$SO-d$_6$-D$_2$O 60$_6$° C.)
δ 0.84 (t, 6H,2MeCH$_2$)
1.23 (s, 52H, 26CH$_2$)
1.83–1.84 (2s, 6H,2 AcN)

EXAMPLE 43

Synthesis of O-(methyl 4-O-acetyl-2-O-benzoyl-3-O-levulinoyl-β-D-glucopyranosyluranate)-(1→3)-O-(2,4,6-tri-O-benzoyl-β-D-galactopyranosyl)-(1→4)-O-(2-acetamido-3,6-di-O-benzoyl-2-deoxy-β-D-glucopyranosyl)-(1→3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3) -O-(2,4,6-tri-O-acetyl-β-D-galactopyranosyl)-(1→4)-O-(2,3,6-tri-O-acetyl-β-D-glucopyranosyl)-(1→1)-(2S, 3R, 4E)-3-O-benzoyl-2-tetracosanamido -4-O-octadecene-1,3-diol (compound 42-B, n=23)

Selective reduction of the azido group of compound 41 (700 mg, 0.23 m mol) and subsequent coupling with tetracosanoic acid) (270 mg, 0.73 m mol), as described in Example 38, gave amorphous comopund 42-B (n=23) (503 mg, 65% yield)

Elementary analysis as $C_{182}H_{223}N_3O_{60}$ Calc. C 64.05 H 6.59 N 1.23 Found C 63.79 11 6.40 N 1.07

$[\alpha]_D$+16.3°0 (c 1.1, CHCl$_3$)

$^1$H-NMR (CDCl$_3$) δ 0.88 (t, 6H,2MeCH$_2$)
1.25 (s, 64H, 32CH$_2$)
1.76 (s, 6H,2 AcN)
1.87–2.09 (9s, 27H,9 AcO )
2.29 (m, 4H, CH$_2$CH$_2$Ac)
3.62 (s, 3H, COOMe) 4.41, 4.48, 4.54, 4.61, 4.68 (5d, 5H, J$_{1,2}$=7.9 ~8.1 Hz, H-1a~g)
5.84 (dt,1H, H-5 for sphingosine)
6.90–8.00 (m, 50H, 10 Ph)
IR (film) 3380 (NH)
2930, 2860 (CH)
1740, 1270 (ester)
1680, 1540 (amide)
760,710,690 cm$^{-1}$ (Ph)

EXAMPLE 44

Synthesis of O-(methyl 4-O-acetyl-2-O-benzoyl-β-D-glucopyranosyluronate) -(1→3)-O-(2,4,6-tri-O-benzoyl-β-D-galactopyranosyl)-(1→4)-O-(2-acetamido-3,6-di-O-benzoyl-2-deoxy-β-D-glucopyranosyl)-(1→3-O-(2,4,6-tri-O-benzoyl-β-D-galactopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl)-(1→4)-O-(2,3,6-tri-O-acetyl-β-D-glucopyranosyl)-(1→1)-(2S,3R, 4E)-3-O-benzoyl-2-tetracosanamido-4-O-octadecene-1,3-diol (compound 43-B, n=23)

Selective removal of the levulinoyl group in compound 42-B (n=23)(290 mg , 85.0 μmol), as described in Example 39, gave amorphous compound 43-B (n=23)(281 mg, quantitative yield):

Elementary analysis as $C_{177}H_{217}N_3O_{58}$ Calc. C 64.14 H 6.60 N 1.27 Found C 64.07 H 6.33 N 1.24

$[\alpha]_D$+9.2° (c 0.5, CHCl$_3$)

$^1$H-NMR (CDl$_3$) δ 0.88 (t, 6H,2MeCH$_2$)
1.26 (s, 64H, 32CH$_2$)
1.78 (s, 6H,2 AcN)
1.99–2.08 (9s, 27H,9 AcO )
3.62 (s, 3H, COOMe)
5.83 (dt,1H, H-5 for sphingosine)
6.93–8.02 (m, 50H, 10 Ph)
IR (film) 3390 (NH, OH)
2930, 2860 (CH)
1750, 1280 (ester)
1680, 1540 (amide)
760,710,690 cm$^{-1}$ (Ph)

EXAMPLE 45

Synthesis of O-(β-D-glucopyranosyluronic acid)-(1→3)-O-(β-D-galactopyranosyl)-(1→4)-O-(2-acetamido-2-deoxy-β-D-glucopyranosyl)-(1→3)-O-(β-D-galactopyranosyl)-(1→4)-O-(2-acetamido-2-deoxy-β-D-glucopyranosyl)-(1→3)-O-(β-D-galactopyranosyl)-(1→4)-O-(β-D-glucopyranosyl)-(1→1)-(2S, 3R, 4E)-2-tetracosanamido-4-octadecene-1,3-diol, sodium salt (compound 45-B, n-23) Deacylation and saponification of compound 43-B (n=23) (130 mg, 39.2 μmol), as described in Example 40, yielded compound 45-B (n=23) (60.5 mg, 82% yield):

$^1$H-NMR (CDCl$_3$) (49:1 Me$_2$SO-d$_6$-D$_2$O, 60$_6$° C.)
δ 0.88 (t, 6H,2MeCH$_2$)
1.25 (s, 64H, 32CH$_2$)

1.87–1.89 (2s, 6H,2 AcN)

EXAMPLE 46

Synthesis of O-(methyl 4-O-acetyl-2-O-benzoyl-3-O-sulfo-β-D-glucopyranosyluronate)-(1→3)-O-(2,4,6-tri-O-benzoyl-β-D-galactopyranosyl)-(1→4)-O-(2-acetamido-3,6-di-O-benzoyl-2-deoxy-β-D-glucopyranosyl)-(1→3)-O-(2,4,6-tri-O-benzoyl-β-D-galactopyranosyl)-(1→4)-O-(2-acetamido-3,6-di-O-acetyl-2-deoxy-β-D-glucopyranosyl)-(1→3)-O-(2,4,6-tri-O-acetyl-β-D-galactopyranosyl)-(1→4)-O-(2,3,6-tri-O-acetyl-β-D-glucopyranosyl)-1→) -(2S,3R,4E)-3-O-benzoyl-2-tetracosanamido-4-O-octadecene-1,3-diol sodium salt (compound 44-B, n=23) Sulfation of compound 43-B(n=23)(274 mg, 82.7 μmol), as described in Example 41, yielded amorphous compound 44-B (n=23)(260 mg, 92% yield):

Elementary analysis as $C_{177}H_{216}N_3O_{16}S_1Na_1$ Calc. C 62.22 H 6.37 N 1.23 Found C 62.03 H 6.13 N 1.09

$[\alpha]_D$+12.3° (c 0.6, $CHCl_3$) $^1$H-NMR ($CDCl_3$) δ 0.88 (t, 6H,2MeCH$_2$)
1.25 (s, 64H, 32C$_2$)
1.85–1.86 (2s, 6H,2 AcN)
1.93–2.09 (9s, 27H, 9 AcO)
3.62 (s, 3H, COOMe)
6.93–8.02 (m, 50H, 10 Ph)
IR (film) 3390 (NH)
2930, 2860 (CH)
1750, 1270 (ester)
1680, 1550 (amide)
760,720,700 cm$^{-1}$ (Ph)

EXAMPLE 47

Synthesis of O-(3-O-sulfo-β-D-glucopyranosyluronic acid))-(1→3)-O -(β-D-galactopyranosyl)-(1→4)-O-(2-acetamido-2-deoxy-β-D-glucopyranosyl) -1→3)-O-(β-D-galactopyranosyl)-(1→4)-O-(2-acetamido)-2-deoxy-β-D-glucopyranosyl)-(1→3)-O-(β-D-galactopyranosyl)-(1→4)-O-(β-D-glucopyranosyl)-(1→1)-(2S, 3R, 4E)-2-tetracosanamido-4-octadecene -1,3-diol, disodium salt (compound 46-B, n=23) Deacylation and saponification of compound 44-B (n=23) (125 mg, 36.6 μmol), as described in Example 40 yielded compound 46-B (n=23) (56.6 mg, 78% yield):

$^1$H-NMR (CDCl$_3$) (49:1 Me$_2$SO-d$_6$-D$_2$O, 60$_6$° C.)
δ0.86 (t, 6H,2MeCH$_2$)
1.26 (s, 64H, 32CH$_2$)
1.83–1.85 (2s, 6H,2 AcN)

BRIEF EXPLANATION OF DRAWINGS

FIG. 1 is a chart showing the synthetic route of methyl (4-O-acetyl-2-O-benzoyl-3-O-levulinoyl-α-D-glucopyranosyl-trichloroacetoimidate uronate (compound 8), which is one of the present intermediate compound for the synthesis of glycolipide.

FIG. 2 is a chart showing the synthetic route of β-D-glucopyranosyluronate -(1→3)-α-D-galactopyranosyl trichloroacetoimide (compound 13), which is one of the present intermediate compound for the synthesis of glycolipide starting from the compound 8.

FIG. 3 is a chart showing the synthetic route of trisaccharide acceptor compound (20) to be used for the synthesis of the present pentasaccharide glycolipide.

FIG. 4 is a chart showing the synthetic route of compound 25, which is useful for the synthesis of the present pentasaccharide glycolipide, starting from compound 13 and (compound 20).

FIG. 5 is a chart showing the synthetic route of pentasaccharide glycolipide s 29 and 30, starting from compound 25 and passing through the present intermediate compounds 26, 27 and 28.

FIG. 6 is a chart showing the synthetic route of compound 35 being useful as an intermediate compound in obtaining a tetra-saccharide donor compound 36 which is useful for the synthesis of the present heptasaccharide glycolipide intermediate compound.

FIG. 7 is a chart showing the synthetic route of compound 40, which is useful for the synthesis of the present heptasaccharide glycolipide, starting from compound 35 and passing through donor compound 36.

FIG. 8 is a chart showing the synthetic route of heptasaccharide glycolipides 45 and 46, starting from compound 40 and passing through the present hepta-saccharide glycolipide intermediate compounds 42, 43 and 44.

What is claimed is:

1. An intermediate compound for the synthesis of glycolipids, represented by the following formula:

wherein $R^1$ is $$-\overset{O}{\underset{\|}{C}}-CH_2CH_2-\overset{O}{\underset{\|}{C}}-CH_3,$$

hydrogen atom or NaO$_3$S—; Ac stands for acetyl group; Me is methyl group; Bz is benzoyl group; and n is an integer of 17 or 23.

2. An intermediate compound for the synthesis of glycolipids, represented by the following formula:

-continued

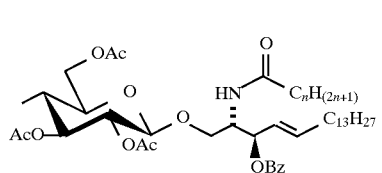

wherein R¹ is

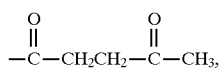

hydrogen atom or NaO$_3$S—; Ac stands for acetyl group; Me is methyl group; Bz is benzoyl group; and n is an integer of 17 or 23.

3. An intermediate compound for the synthesis of glycolipids, represented by the following formula:

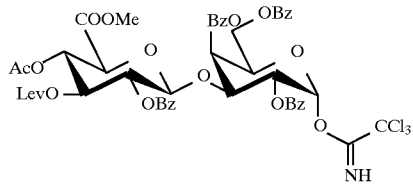

wherein Lev stands for

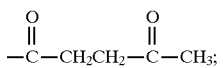

Ac is acetyl group; Me is methyl group and Bz is benzoyl group.

4. An intermediate compound for the synthesis of glycolipids, represented by the following formula:

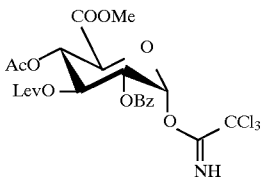

wherein Lev stands for

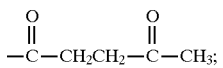

Ac is acetyl group; Me is methyl group and Bz is benzoyl group.

* * * * *